(12) United States Patent
Bellacosa et al.

(10) Patent No.: US 10,220,051 B2
(45) Date of Patent: Mar. 5, 2019

(54) COMBINATION OF DNA REPAIR INHIBITION WITH BENDAMUSTINE OR GEMCITABINE IN THE TREATMENT OF CANCER

(71) Applicant: Institute for Cancer Research, Philadelphia, PA (US)

(72) Inventors: Alfonso Bellacosa, Philadelphia, PA (US); Timothy Yen, Haverford, PA (US); Neil Beeharry, Philadelphia, PA (US); Mitchell Smith, Elkins Park, PA (US); Rossella Tricarico, Philadelphia, PA (US); Vikram Bhattacharjee, Philadelphia, PA (US); Pietro Mancuso, Philadelphia, PA (US)

(73) Assignee: Institute For Cancer Research

( * ) Notice: Subject to any disclaimer, the term of this patent is extended or adjusted under 35 U.S.C. 154(b) by 0 days.

(21) Appl. No.: 14/540,428

(22) Filed: Nov. 13, 2014

(65) Prior Publication Data

US 2015/0164934 A1 Jun. 18, 2015

Related U.S. Application Data

(63) Continuation-in-part of application No. 13/836,414, filed on Mar. 15, 2013, now Pat. No. 8,927,516.

(60) Provisional application No. 61/617,427, filed on Mar. 29, 2012.

(51) Int. Cl.

| A61K 31/7068 | (2006.01) |
| A61K 31/4184 | (2006.01) |
| A61K 31/122 | (2006.01) |
| A61K 31/546 | (2006.01) |
| A61K 31/277 | (2006.01) |
| A61K 31/7088 | (2006.01) |
| C12N 15/113 | (2010.01) |

(52) U.S. Cl.
CPC ........ *A61K 31/7068* (2013.01); *A61K 31/122* (2013.01); *A61K 31/277* (2013.01); *A61K 31/4184* (2013.01); *A61K 31/546* (2013.01); *A61K 31/7088* (2013.01); *C12N 15/1137* (2013.01); *C12N 2310/14* (2013.01); *C12N 2320/31* (2013.01); *C12Y 302/02029* (2013.01)

(58) Field of Classification Search
CPC .............. A61K 31/122; A61K 31/7068; A61K 31/4184; A61K 31/546; A61K 31/277
See application file for complete search history.

(56) References Cited

U.S. PATENT DOCUMENTS

| 2003/0139363 A1 | 7/2003 | Kay et al. |
| 2003/0229004 A1 | 12/2003 | Zarling et al. |
| 2006/0128777 A1 | 6/2006 | Bendall et al. |
| 2006/0142231 A1 | 6/2006 | Ashworth et al. |
| 2006/0241186 A1 | 10/2006 | Gerson et al. |
| 2013/0303588 A1 | 11/2013 | Bellacosa et al. |

OTHER PUBLICATIONS

Peters et al. Pharmacology & Therapeutics, 2000, vol. 87, pp. 227-253.*
Aithal et al. Cell Biology International, 2009, vol. 33, pp. 1039-1049.*
Montenegro et al. Chemico-Biological Interactions, 2010, vol. 184, pp. 439-448.*
Aithal et al. Integrative Cancer Therapies, 2012, vol. 11, No. 1, pp. 68-80.*
Xu et al. Bioorganic & Medicinal Chemistry Letters, 2013, vol. 23, pp. 3631-3634.*
Cortazar et al. DNA Repair, 2007, vol. 6, pp. 489-504.*
Boorstein, R.J., et al., "Definitive Identification of Mammalian 5-Hydroxymethyluracil DNA N-Glycosylase Activity as SMUG1," J. Biol. Chem., vol. 276, No. 45 (Nov. 9, 2001), pp. 41991-41997.
Burris, H.A., et al., "Improvements in Survival and Clinical Benefit with Gemcitabine as First-Line Therapy for Patients with Advanced Pancreas Cancer: A Randomized Trial", J. Clin. Oncol., vol. 15, No. 6, Jun. 1997, pp. 2403-2413.
Cortellino, S., et al., "Thymine DNA Glycosylase is Essential for Active DNA Demethylation by Linked Deamination-Base Excision Repair", Cell, 146, 2011, pp. 67-79.
Kunz, C., et al., "Base Excision by Thymine DNA Glycosylase Mediates DNA-Directed Cytotoxicity of 5-Fluorouracil," PLoS Biology, vol. 7, Issue 4 (Apr. 2009), pp. 0967-0979.
Leoni, L., et al., "Bendamustine (Treanda) Displays a Distinct Pattern of Cytotoxicity and Unique Mechanistic Features Compared with other Alkylating Agents", Clin. Cancer Res., 2008; 14(1), Jan. 1, 2008, pp. 309-317.
Mini, E., et al., "Cellular pharmacology of gemcitabine," Ann. Oncol. 17, Suppl. 5:v7-12, 2006.
Petronzelli, F., et al., "Biphasic Kinetics of the Human DNA REpair Protein MED1 (MBD4), a Mismatch-specific DNA N-Glycosylase," J. Biol. Chem., vol. 275, No. 42, (Oct. 20, 2000) pp. 32422-32429.
Vilpo, J.A., et al., "Metabolism, Incorporation into DNA, and Interactions with 1-beta-D-arabinofuranosylcytosine of 5-hydroxymethyl-2'-deoxyuridine in human promyelocytic leukemia cells (HL-60)1," Cancer Res., 48:3117-22, 1988.
Aithal, et al., "Evaluation of pharmacokinetic, biodistribution, pharmacodynamic, and toxicity profile of free juglone and its sterically stabilized liposomes", Journal of Pharmaceutical Sciences, vol. 100, No. 8, Aug. 2011, pp. 3517-3528.

(Continued)

*Primary Examiner* — James D. Anderson
(74) *Attorney, Agent, or Firm* — Stradley Ronon Stevens & Young, LLP

(57) ABSTRACT

The invention provides methods for enhancing the cytotoxicity of DNA damage in cancer cells that express thymine DNA glycosylase, and treating tumors accordingly. The methods comprise inhibiting the expression or biologic activity of thymine DNA glycosylase, and inducing DNA damage in the cancer cells. DNA damage may be induced by administration of bendamustine or gemcitabine to the cancer cells.

12 Claims, 23 Drawing Sheets

Specification includes a Sequence Listing.

(56) References Cited

OTHER PUBLICATIONS

Awada, et al., "Prolonged Schedule of Temozolomide (Temodal) plus liposomal doxorubicin (Caelyx) in advanced solid cancers", Anti-Cancer Drugs, vol. 15, No. 5, Jun. 2004, pp. 499-502.

Ji, et al., "Juglone-induced apoptosis in human gastric cancer SGC-7901 cells via the mitochondrial pathway", Experimental and Toxicologic Pathology, vol. 63, No. 1-2, Jan. 1, 2011, pp. 69-78.

Kumar, et al., "Cytotoxic, genotoxic and oxidative stress induced by 1,4-naphthoquinone in B16F1 melanoma tumor cells", Toxicology in Vitro, vol. 23, No. 2, Mar. 1, 2009, pp. 242-250.

Zhang, et al., "Anticancer activity and mechanism of juglone on human cervical carcinoma HeLa cells", Canadian Journal of Physiology and Pharmacology, vol. 90, No. 11, Nov. 2012, pp. 1553-1558.

Supplementary Partial European Search Report issued in related application EP14847598 dated Aug. 18, 2016.

\* cited by examiner

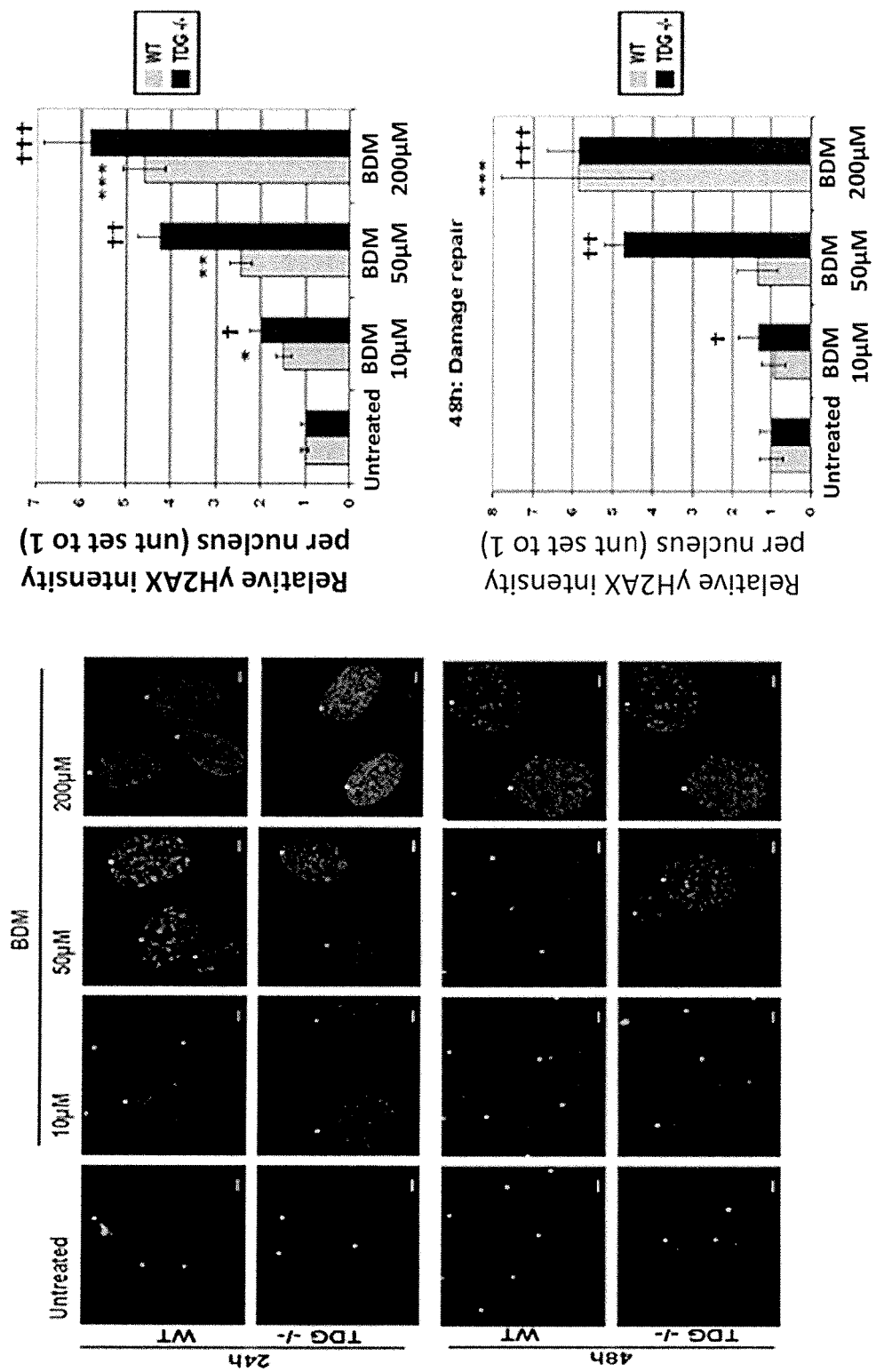

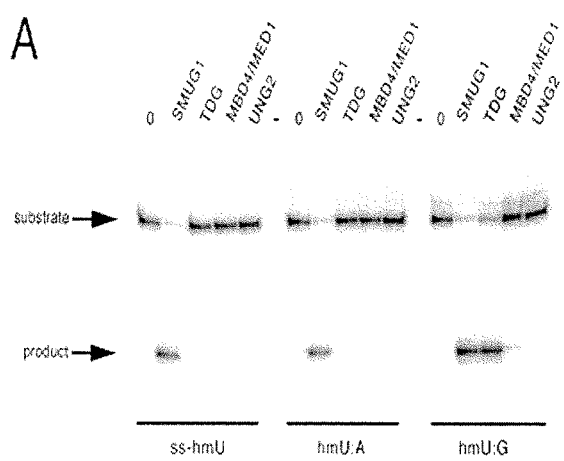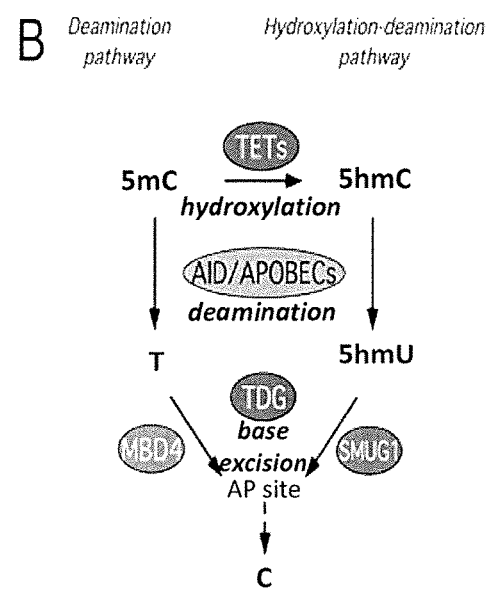
Figure 8A
Figure 8B

COMBINATION OF DNA REPAIR INHIBITION WITH BENDAMUSTINE OR GEMCITABINE IN THE TREATMENT OF CANCER

CROSS REFERENCE TO RELATED APPLICATIONS

This application is a continuation-in-part of U.S. application Ser. No. 13/836,414, which was filed on Mar. 13, 2013, and claims priority to U.S. Provisional Application No. 61/617,427, filed on Mar. 29, 2012, the contents of each application are incorporated by reference herein, in their entirety and for all purposes.

REFERENCE TO GOVERNMENT GRANTS

This invention was made with government support under Grant Nos. GM86877 and CA078412 awarded by the National Institutes of Health and Grant No. W81XWH-11-1-0201 awarded by the U.S. Department of Defense ARMY/MRMC. The government has certain rights in the invention.

REFERENCE TO A SEQUENCE LISTING

This application includes a Sequence Listing submitted electronically as a text file named TDG_ST25.txt, created on Mar. 12, 2013 with a size of 1,000 bytes. The Sequence Listing is incorporated by reference herein.

FIELD OF THE INVENTION

The invention relates generally to the field of cancer treatment. More particularly, the invention relates to combination therapies for treating cancer cells, and especially for enhancing the susceptibility of cancer cells to chemotherapeutic agents such as bendamustine and gemcitabine with inhibitors of TDG such as juglone, cefixime, and closantel.

BACKGROUND OF THE INVENTION

Various publications, including patents, published applications, technical articles and scholarly articles are cited throughout the specification. Each of these cited publications is incorporated by reference herein, in its entirety and for all purposes.

Bendamustine (BDM) represents one of the earliest rationally designed anticancer drugs that incorporated three functional groups, a benzimidazole ring, a mechlorethamine group and a butanoic acid residue. These groups putatively endowed BDM with both alkylator and antimetabolite activities. BDM has been found to be especially effective in hematologic-related cancers including chronic lymphocytic leukemia (CLL) and indolent B-cell non-Hodgkin lymphoma (NHL) for which the FDA has approved its use, and multiple myeloma. The differences in the expression pattern of genes involved in DNA-damage stress response, apoptosis, cell cycle, mitosis and DNA replication after treatment with BDM and standard alkylating agents suggested that BDM elicits a different cytotoxic response mediated by a mechanism of action that differs from other alkylating agents.

The deoxycytidine analogue gemcitabine (2',2'-difluorodeoxycytidine, a.k.a. Gem) is an antimetabolite used for the treatment of advanced pancreatic, lung, bladder and breast cancer. In particular, Gem is the drug of choice for metastatic pancreatic cancer, but it only exhibits a modest increase (months) in overall survival and amelioration of symptoms in comparison to 5-fluorouracil. Gem is an ideal candidate for combination chemotherapy due to the lack of cross-resistance with other agents. On the other hand, inter-patient variability of anti-tumor activity and toxicity, and ultimately development of resistance, underscore the need to improve Gem efficacy.

SUMMARY OF THE INVENTION

The invention features methods for enhancing the sensitivity of tumor cells to gemcitabine, and for enhancing the sensitivity of tumor cells to bendamustine. The methods comprise contacting the cells with an amount of gemcitabine or an amount of bendamustine that is effective to induce sustained S phase cell cycle arrest in the tumor cells, and inhibiting the expression or the biologic activity of thymine DNA glycosylase (TDG) in tumor cells. The methods may be used to enhance the sensitivity of a tumor cell that expresses TDG and, ultimately, kill the tumor cells. It is believed that bendamustine and gemcitabine may be used in this way to induce significant DNA damage in the tumor cells, and TDG inhibitors may be used to inhibit attempts by the cell to repair this DNA damage. Tumor cells that may be treated in this way include tumor cells of the pancreas, lung, kidney, breast, colon, ovary, lymph nodes, bladder, prostate gland, head and neck, stomach, skin, esophagus, or hematopoietic system, and potentially other tumor cell types. The inhibitor may allow lower doses of gemcitabine and bendamustine to be used, and thereby expand their effectiveness against other tumor types, which may be insufficiently sensitive to low doses of gemcitabine or bendamustine in the absence of inhibition of the expression or the biologic activity of TDG. The methods may be carried out in vivo, in vitro, or in situ.

In some detailed aspects, the methods comprise contacting tumor cells with an amount of bendamustine or gemcitabine effective to induce sustained S phase arrest in the cells, and then inhibiting the biologic activity of thymine DNA glycosylase (TDG) in the cells by contacting the cells with an amount of a TDG inhibitor that is effective to inhibit the biologic activity of TDG in the cells. Inhibiting the biologic activity of TDG in the cells enhances bendamustine-induced or gemcitabine-induced sustained S phase arrest in the cells relative to the level of bendamustine-induced or gemcitabine-induced sustained S phase arrest in tumor cells of the same type in which the biologic activity of TDG was not inhibited. The TDG inhibitor may comprise juglone, cefixime, closantel, or a combination thereof. Preferred tumor cells include melanoma cells, breast cancer cells, and pancreatic cancer cells.

The invention also features methods for treating tumors. Non-limiting examples of tumors that may be treated include a tumor of the pancreas, tumor of the lung, tumor of the kidney, tumor of the breast, tumor of the colon, tumor of the ovary, tumor of the lymph nodes, tumor of the bladder, tumor of the prostate gland, a tumor of the head and neck, a tumor of the stomach, a tumor of the esophagus, a tumor of the skin (e.g., melanoma), and a tumor of the hematopoietic system. In general, the methods comprise administering to the tumor an effective amount of bendamustine or gemcitabine in combination with an effective amount of a TDG inhibitor. The TDG inhibitor preferably comprises juglone, cefixime, closantel, or a combination thereof. Preferred tumors include melanoma, breast cancer, and pancreatic cancer.

In some detailed aspects, the method comprises administering to a tumor of the pancreas, including by administering to a pancreatic cancer patient in need thereof, an effective amount of bendamustine or gemcitabine in combination with an effective amount of a TDG inhibitor selected from the group consisting of juglone, closantel, and cefixime, such that the bendamustine or gemcitabine induces sustained S phase arrest in tumor cells of the pancreas, and the TDG inhibitor inhibits TDG in the tumor cells sufficient to induce death of the tumor cells, thereby treating the tumor of the pancreas. In some aspects, both bendamustine and gemcitabine may be administered. Administration may be according to any suitable technique and route. In some aspects, DNA damage may be induced in the tumor by radiation, in lieu of administration of bendamustine or gemcitabine. Thus, radiation-induced DNA damage may be used in combination with juglone, closantel, or cefixime. It is preferred that such DNA damage is sufficient to induce S phase cell cycle arrest in the tumor cells.

In some detailed aspects, the method comprises administering to a tumor of the breast, including by administering to a breast cancer patient in need thereof, an effective amount of bendamustine or gemcitabine in combination with an effective amount of a TDG inhibitor selected from the group consisting of juglone, closantel, and cefixime, such that the bendamustine or gemcitabine induces sustained S phase arrest in tumor cells of the breast, and the TDG inhibitor inhibits TDG in the tumor cells sufficient to induce death of the tumor cells, thereby treating the tumor of the breast. In some aspects, both bendamustine and gemcitabine may be administered. Administration may be according to any suitable technique and route. In some aspects, DNA damage may be induced in the tumor by radiation, in lieu of administration of bendamustine or gemcitabine. Thus, radiation-induced DNA damage may be used in combination with juglone, closantel, or cefixime. It is preferred that such DNA damage is sufficient to induce S phase cell cycle arrest in the tumor cells.

In some detailed aspects, the method comprises administering to a melanoma tumor, including by administering to a melanoma patient in need thereof, an effective amount of bendamustine or gemcitabine in combination with an effective amount of a TDG inhibitor selected from the group consisting of juglone, closantel, and cefixime, such that the bendamustine or gemcitabine induces sustained S phase arrest in melanoma cells, and the TDG inhibitor inhibits TDG in the tumor cells sufficient to induce death of the tumor cells, thereby treating the melanoma. In some aspects, both bendamustine and gemcitabine may be administered. Administration may be according to any suitable technique and route. In some aspects, DNA damage may be induced in the tumor by radiation, in lieu of administration of bendamustine or gemcitabine. Thus, radiation-induced DNA damage may be used in combination with juglone, closantel, or cefixime. It is preferred that such DNA damage is sufficient to induce S phase cell cycle arrest in the tumor cells.

In some detailed aspects, the method comprises administering to a tumor of the colon, including by administering to a colon cancer patient in need thereof, an effective amount of bendamustine or gemcitabine in combination with an effective amount of a TDG inhibitor selected from the group consisting of juglone, closantel, and cefixime, such that the bendamustine or gemcitabine induces sustained S phase arrest in tumor cells of the colon, and the TDG inhibitor inhibits TDG in the tumor cells sufficient to induce death of the tumor cells, thereby treating the tumor of the colon. In some aspects, both bendamustine and gemcitabine may be administered. Administration may be according to any suitable technique and route. In some aspects, DNA damage may be induced in the tumor by radiation, in lieu of administration of bendamustine or gemcitabine. Thus, radiation-induced DNA damage may be used in combination with juglone, closantel, or cefixime. It is preferred that such DNA damage is sufficient to induce S phase cell cycle arrest in the tumor cells.

BRIEF DESCRIPTION OF THE DRAWINGS

FIG. 2A shows immunofluorescence analysis performed to identify γ-H2AX, 53BP1 or RPA. Quantification of the average fluorescence per nucleus is shown on the right. For γ-H2AX: *$P=8.9 \times 10^{-28}$ vs. untreated 24 h; **$P=2.1 \times 10^{-31}$ vs. untreated 24 h; †$P=5.2 \times 10^{-45}$ vs. untreated 48 h. For 53BP1: *$P=4.3 \times 10^{-20}$ vs. untreated 24 h; **$P=4.2 \times 10^{-41}$ vs. untreated 24 h; †$P=2.0 \times 10^{-52}$ vs. untreated 48 h. For RPA: *$P=2.5 \times 10^{-16}$ vs. untreated 24 h; **$P=2.8 \times 10^{-52}$ vs. untreated 24 h; †$P=3.3 \times 10^{-58}$ vs. untreated 48 h. FIG. 2B shows lysates probed to determine p-Chk1 (Ser345). Total Chk1 and alpha tubulin were used to determine loading. FIG. 2C shows cell cycle profiles determined by FACs analysis.

FIGS. 3A and 3B show bendamustine-induced DNA damage activates base excision repair. FIG. 3A shows immunofluorescence analyses performed to detect remaining γ-H2AX after 48 h continuous treatment with 50 µM BDM in the presence or absence of either methoxyamine (MX) (6 mM) or the DNA PK inhibitor NU7441 (10 µM). Representative images are shown (left) along with quantitative analysis (right). Average values±SD are shown. *$P<0.005$ vs. BDM alone. FIG. 3B shows DNA damage induction and repair was conducted in assessed mouse embryo fibroblast (MEFs) (WT and TDG$^{-/-}$) after treatment with BDM at 50 or 200 µM BDM for 24 h or 48 h. Representative images are shown, with nuclei outlined (circles) based on DAPI staining. Average γ-H2AX signal per nucleus±SD is quantified (right). 24 h: *$p=0.009$, $p=2.0 \times 10^{-8}$, *$p=4.7 \times 10^{-18}$ vs. untreated WT; †$p=0.00015$, $p=2.8 \times 10^{-11}$, *$p=5.2 \times 10^{-10}$ vs. untreated TDG$^{-/-}$. 48 h: *$p=4.1 \times 10^{-10}$ vs. untreated WT; †$p=0.009$, $p=1.4 \times 10^{-16}$, ***$p=1.9 \times 10^{-16}$ vs. untreated TDG$^{-/-}$.

FIG. 4A shows clonogenic assays performed to assess cell survival following BDM and Chk1 inhibition. Hela cells were treated with BDM (50 or 200 µM) for 24 h. Cells were grown for ~10 days before being fixed and stained. The data presented is the mean absorbance value (O.D. 595 nm) relative to untreated cells, which is set to 100%. Each bar graph represents the average of 3 individual experiments performed in triplicate±SD. †$P<0.05$ or *$P<0.0001$ or vs. untreated cells. FIG. 4B shows cell viability assessed by MTS assay was performed. Hela cells were treated with bendamustine (3.125-200 µM) for 24 h. After this time, appropriate wells were co-treated with UCN-01 (100 nM) or Chk2 inhibitor (100 nM) for an additional 24 h. Data represent the mean of 3 individual experiments performed in triplicate. Cell viability is expressed as a percentage of untreated cells±SD. *P<0.0001 vs. 200 μM BDM alone. FIG. 4C shows the percentage of apoptotic cells following indicated drug treatments determined using Guava Nexin Reagent™. Data represent the average of 3 individual experiments±SD. *P<0.01 vs. untreated viable cells; †P<0.01 vs. untreated apoptotic cells.

FIG. 5A shows a representative montage of cells progressing through mitosis after mock treatment (upper panel), BDM at 50 μM (middle) or 200 μM (lower) followed by UCN-01 addition. FIG. 5B shows mitotic cells fixed for metaphase spreads and dispersed onto glass slides, allowed to dry and then stained with DAPI. Metaphases were visualized using a fluorescence microscopy. Images shown are representative of metaphases observed under each experimental condition. FIG. 5C. shows representative electron micrographs of mitotic cells generated from untreated, 50 μM or 200 μM BDM+UCN-01 treatments. FIG. 5D shows cell cycle data quantitatively.

FIGS. 8A and 8B show TDG glycosylase activity on hmU and model of the role of TDG in DNA demethylation pathways. FIG. 8A shows recombinant TDG and related glycosylases were incubated with hmU-containing single-strand oligonucleotide or double-strand oligonucleotides bearing hmU:A pairing or hmU:G mismatch, all $^{32}$P labeled on the hmU strand. The resulting AP site was cleaved with alkali at high temperature. FIG. 8B shows a schematic of the involvement of TDG in both the deamination and hydroxylation-deamination pathways of DNA demethylation.

DETAILED DESCRIPTION OF THE INVENTION

Figure 1A:
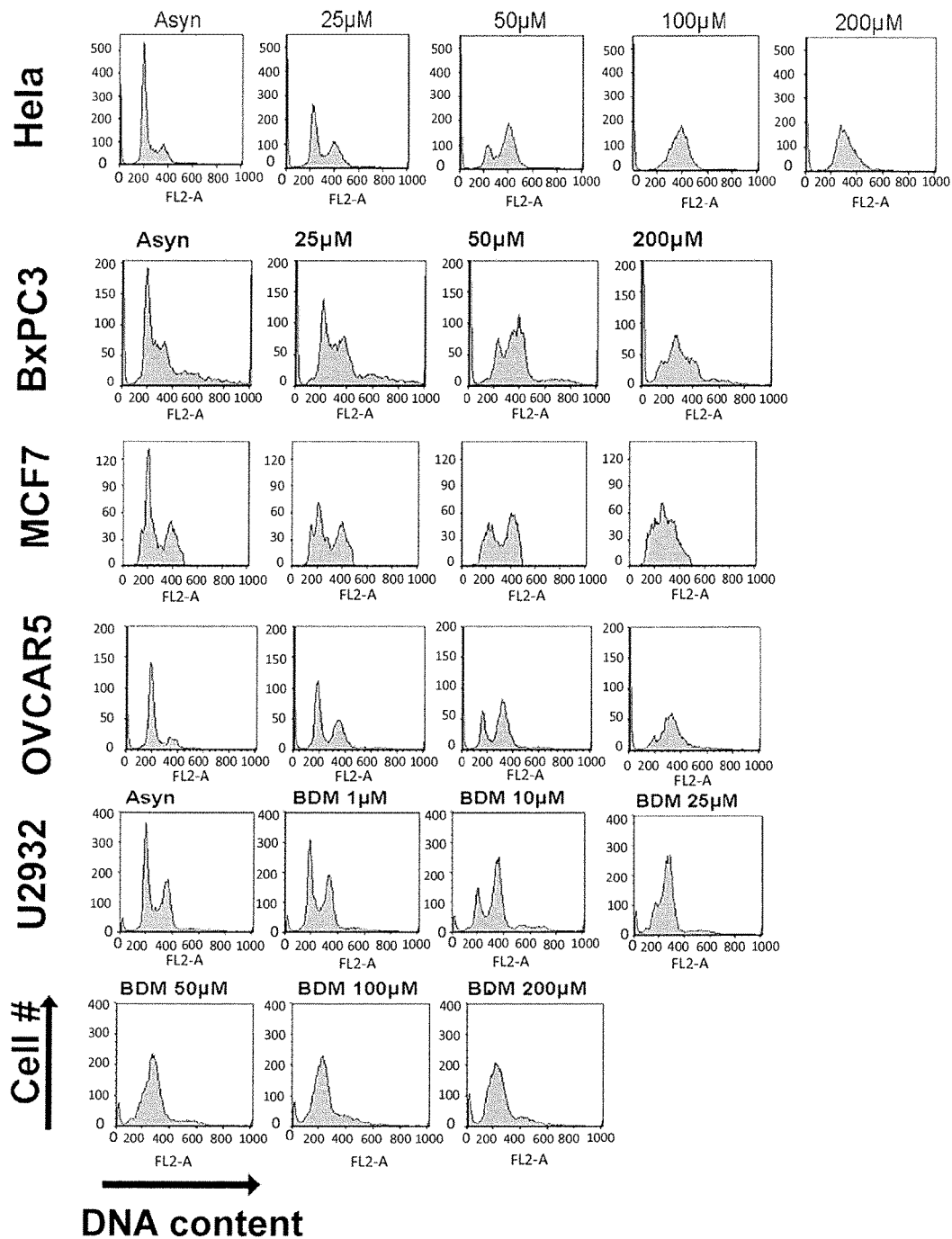
FIG. 1A and FIG. 1B shows that cell cycle perturbations induced by bendamustine is a widespread phenomenon in cancer cell lines. Hela, BXPC3, MCF7, OVCAR 5 and U2932 cells were treated with bendamustine at the indicated concentrations for 24 h. Cell cycle profiles were determined using FACs analysis.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

Knockdown includes the reduced expression of a gene. A knockdown typically has at least about a 20% reduction in expression, preferably has at least about a 50% reduction in expression, and more preferably has at least about a 75% reduction in expression, and in some aspects has at least about an 80% to about an 85% reduction in expression, at least about an 85% to about a 90% reduction in expression, or about an 80% to about a 90% reduction in expression, and in some aspects has a greater than 90% reduction in expression, or a greater than 95% reduction in expression.

Transforming a cell includes the introduction of exogenous or heterologous nucleic acid molecules into the cell. Cells may be stably or transiently transformed.

Nucleic acid molecules include any chain of at least two nucleotides, which may be unmodified or modified RNA or DNA, hybrids of RNA and DNA, and may be single, double, or triple stranded.

Expression of a nucleic acid molecule comprises the biosynthesis of a gene product. Expression includes the transcription of a gene into RNA, the translation of RNA into a protein or polypeptide, and all naturally occurring post-transcriptional and post-translational modifications thereof.

Bendamustine comprises a compound having Formula I, and all pharmaceutically acceptable salts thereof. Formula I:

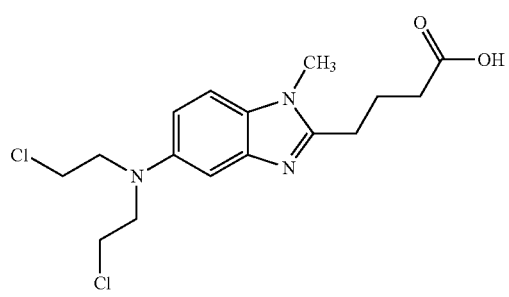 [SMILES: Cn1c(CCCC(=O)O)nc2cc(N(CCCl)CCCl)ccc21]

Gemcitabine comprises a compound having Formula II, and all pharmaceutically acceptable salts thereof. Formula II:

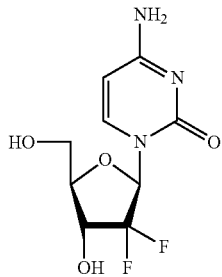 [SMILES: Nc1ccn([C@@H]2O[C@H](CO)[C@H](O)C2(F)F)c(=O)n1]

Juglone (5-hydroxynaphthoquinone) comprises a compound having Formula III, and all pharmaceutically acceptable salts thereof. Formula III:

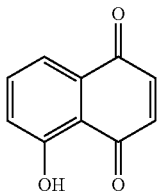 [SMILES: O=C1C=CC(=O)c2c(O)cccc21]

Cefixime ((6R,7R)-7-{[2-(2-amino-1,3-thiazol-4-yl)-2-(carboxymethoxyimino)acetyl]amino}-3-ethenyl-8-oxo-5-thia-1-azabicyclo[4.2.0]oct-2-ene-2-carboxylic acid) comprises a compound having Formula IV, and all pharmaceutically acceptable salts thereof. Formula IV:

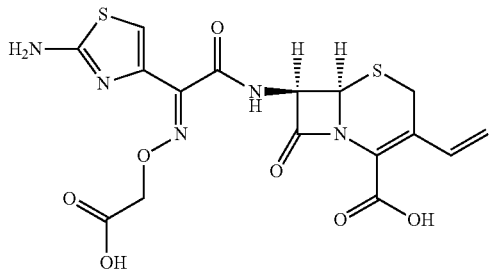 [SMILES: C=CC1=C(C(=O)O)N2C(=O)[C@@H](NC(=O)/C(=N/OCC(=O)O)c3csc(N)n3)[C@H]2SC1]

Closantel (5'-Chloro-4'-(4-chloro-α-cyanobenzyl)-3,5-diiodo-2'-methylsalicylanilide, N-[5-Chloro-4-(4-chloro-α-cyanobenzyl)-2-methylphenyl]-2-hydroxy-3,5-diiodobenzamide) comprises a compound having Formula V, and all pharmaceutically acceptable salts thereof. Formula V:

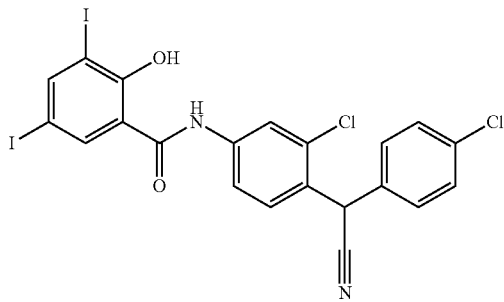 [SMILES: N#CC(c1ccc(Cl)cc1)c1ccc(NC(=O)c2cc(I)cc(I)c2O)cc1Cl]

Inhibiting or interfering includes reducing, decreasing, blocking, preventing, delaying, inactivating, desensitizing, stopping, knocking down (e.g., knockdown), and/or down-regulating the biologic activity or expression of a molecule or pathway of interest.

Pharmaceutically acceptable salts may be acid or base salts. Non-limiting examples of pharmaceutically acceptable salts include sulfates, methosulfates, methanesulfates, pyrosulfates, bisulfates, sulfites, bisulfites, nitrates, besylates, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, dioates, benzoates, chlorobenzoates, methylbenzoates, dinitromenzoates, hydroxybenzoates, methoxybenzoates, phthalates, sulfonates, toluenesulfonates, xylenesulfonates, pheylacetates, phenylpropionates, phenylbutyrates, citrates, lactates, γ-hydroxybutyrates, glycollates, tartrates, methanesulfonates, propanesulfonates, mandelates, and other salts customarily used or otherwise FDA-approved.

It has been observed in accordance with the invention that inhibition of the DNA mismatch repair enzyme thymine DNA glycosylase (TDG) sensitizes cancer cells to bendamustine treatment and to gemcitabine treatment. It has also been observed that the agent bendamustine affects cell cycle arrest in a dose-dependent manner, such that high levels of bendamustine-induced DNA damage cannot be sufficiently repaired. It was further observed that chemical TDG inhibitors (e.g., closantel, juglone, and cefixime) can synergize with bendamustine and with gemcitabine for enhanced cell death over either the TDG inhibitor or bendamustine or gemcitabine alone. These observations indicate that induction of high levels of DNA damage in cancer cells, coupled with inhibition of the cells' ability to correct the damage can enhance cell death as well as increase the sensitivity of cancer cells to DNA damage and to chemotherapeutic agents. Accordingly, the invention features methods for enhancing the sensitivity of cancer cells to chemotherapeutic agents, and for treating tumors accordingly. In general, the methods comprise combining the inhibition of DNA mismatch repair and base excision repair enzymes such as TDG with the induction of DNA damage. Any of the methods of the invention may be carried out in vivo, in vitro, or in situ.

In some aspects, the invention provides methods for enhancing the sensitivity of a tumor cell to DNA damage and DNA damage-induced cell death. The methods may comprise inhibiting the expression or inhibiting the biologic activity of thymine DNA glycosylase (TDG) in the cell and damaging DNA in the cell, particularly damaging DNA at levels of that the cell may not be able to repair with other DNA repair enzymes. Damaging DNA may comprise irradiating the cell, or may comprise contacting the cell with an effective amount of an agent that induces DNA damage. Inhibiting the expression or the biologic activity of TDG in the cell enhances the sensitivity of the cell to cell death induced by DNA damage relative to the level of DNA damage-induced cell death in a cell in which the expression or the biologic activity of TDG was not inhibited.

In some detailed aspects, the invention provides methods for enhancing the sensitivity of a tumor cell to gemcitabine. The methods may comprise inhibiting the expression or inhibiting the biologic activity of TDG in the cell, and contacting the cell with an effective amount of gemcitabine. Inhibiting the expression or the biologic activity of TDG in the cell enhances the sensitivity of the cell to gemcitabine-induced cell death relative to the level of gemcitabine-induced cell death in a cell contacted with gemcitabine in which the expression or the biologic activity of TDG was not inhibited. The methods may further comprises contacting the cell with an effective amount of 5-hydroxymethyl-2'-deoxyuridine.

In some detailed aspects, the invention provides methods for enhancing the sensitivity of a tumor cell to bendamustine. The methods may comprise inhibiting the expression or inhibiting the biologic activity of TDG in the cell, and contacting the cell with an effective amount of bendamustine. Inhibiting the expression or the biologic activity of TDG in the cell enhances the sensitivity of the cell to bendamustine-induced cell death relative to the level of bendamustine-induced cell death in a cell contacted with bendamustine in which the expression or the biologic activity of TDG was not inhibited. The methods may further comprises contacting the cell with an effective amount of 5-hydroxymethyl-2'-deoxyuridine.

The methods may be used to enhance the sensitivity of any tumor cell to DNA damage and DNA damage-induced cell death, as well as to enhance the sensitivity of any tumor cell to gemcitabine or to bendamustine. The tumor cell may be a tumor cell that expressed TDG. For example, the tumor cell may be a tumor cell of the pancreas, a tumor cell of the head and neck, a tumor cell of the lung, a tumor cell of the kidney, a tumor cell of the breast, a tumor cell of the colon, a tumor cell of the ovary, a tumor cell of a lymph node, a tumor cell of the bladder, a tumor cell of the prostate gland, a tumor cell of the stomach, a tumor cell of the esophagus, a tumor cell of the skin (e.g., melanoma cell), or a tumor cell of the hematopoietic system. The tumor cell may be from any organism, including mammals such as farm animals (e.g., horse, cow, sheep, pig), laboratory animals (e.g., mouse, rat, rabbit), companion animals (e.g., dog, cat), and non-human primates (e.g., new world monkey and old world monkey). In preferred aspects, the tumor cell is from a human being.

It is believed that the methods may find use in sensitizing a tumor cell to low doses of gemcitabine or bendamustine. For example, it is believed that inhibition the expression or the biologic activity of TDG may allow the use of lower doses (e.g., sub-therapeutic doses) of gemcitabine and bendamustine. Use of lower doses of these drugs may thus reduce the toxicity of these drugs in a subject, and thereby allow them to be used on tumor cells that would not be sensitive to low doses of gemcitabine and bendamustine in the absence of the inhibition of the expression or the biologic activity of TDG.

Biologic activity of TDG includes DNA/thymine glycosylase activity and excision repair of thymine and uracil mismatches, including G/T, G/U, C/T, and T/T mismatches, as well as repair of hydroxymethyluracil, formylcytosine and carboxylcytosine opposite G. Biologic activity also includes transcriptional co-activator activity. In some aspects, it may be preferable to selectively inhibit glycosylase activity, for example, while retaining transcriptional co-activator activity. In some aspects, it may be preferable to selectively inhibit transcriptional co-activator activity, for example, while retaining glycosylase activity.

Inhibiting the biologic activity of TDG may comprise contacting the cell with an effective amount of an agent that inhibits the biologic activity of TDG. The agent may comprise an organic or inorganic chemical (including a composition comprising such an organic or inorganic chemical, including a small molecule, and a carrier such as a pharmaceutically acceptable carrier) that inhibits the biologic activity of TDG. Suitable agents include, for example, juglone, closantel, and cefixime, and pharmaceutically acceptable salts thereof. Such TDG-inhibiting agents may be used in combination with each other (e.g., juglone with closantel, juglone with cefixime, or closantel and cefixime).

Inhibiting the expression of TDG may comprise transforming the tumor cell with a nucleic acid molecule that interferes with the expression of TDG. For example, nucleic acid-based interference with TDG expression may take advantage of RNA interference.

RNA interference (RNAi) is a mechanism of post-transcriptional gene silencing mediated by double-stranded RNA (dsRNA), which is distinct from antisense and ribozyme-based approaches. RNA interference may be effectuated, for example, by administering a nucleic acid (e.g., dsRNA) that hybridizes under stringent conditions to the gene encoding thymine DNA glycosylase (including mRNA encoding thymine DNA glycosylase), thereby attenuating its expression. RNA interference provides shRNA or siRNA that comprise multiple sequences that target one or more regions of the target gene. dsRNA molecules (shRNA or siRNA) are believed to direct sequence-specific degradation of mRNA in cells of various types after first undergoing processing by an RNase III-like enzyme called DICER into smaller dsRNA molecules comprised of two 21 nucleotide (nt) strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

Viral vectors or DNA vectors encode short hairpin RNA (shRNA) which are processed in the cell cytoplasm to short interfering RNA (siRNA). In general, a short, interfering RNA (siRNA) comprises an RNA duplex that is preferably approximately 19 basepairs long and optionally further comprises one or two single-stranded overhangs or loops. A siRNA may comprise two RNA strands hybridized together, or may alternatively comprise a single RNA strand that includes a self-hybridizing portion. siRNAs may include one or more free strand ends, which may include phosphate and/or hydroxyl groups. siRNAs typically include a portion that hybridizes under stringent conditions with a target transcript. One strand of the siRNA (or, the self-hybridizing portion of the siRNA) is typically precisely complementary with a region of the target transcript (e.g., thymine DNA glycosylase transcript), meaning that the siRNA hybridizes to the target transcript without a single mismatch. In aspects in which perfect complementarity is not achieved, it is generally preferred that any mismatches be located at or near the siRNA termini.

siRNAs have been shown to downregulate gene expression when transferred into mammalian cells by such methods as transfection, electroporation, cationic liposome-mediated transfection, or microinjection, or when expressed in cells via any of a variety of plasmid-based approaches. The siRNA may comprise two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is believed that intracellular processing (e.g., by DICER) of a variety of different precursors results in production of siRNA capable of effectively mediating gene silencing. Generally, it is preferred to target exons rather than introns, and it may also be preferable to select sequences complementary to regions within the 3' portion of the target transcript. Generally it is preferred to select sequences that contain an approximately equimolar ratio of the different nucleotides and to avoid stretches in which a single residue is repeated multiple times.

siRNAs may thus comprise RNA molecules having a double-stranded region approximately 19 nucleotides in length with 1-2 nucleotide 3' overhangs on each strand, resulting in a total length of between approximately 21 and 23 nucleotides. siRNAs also include various RNA structures that may be processed in vivo to generate such molecules. Such structures include RNA strands containing two complementary elements that hybridize to one another to form a stem, a loop, and optionally an overhang, preferably a 3' overhang. Preferably, the stem is approximately 19 bp long, the loop is about 1-20, more preferably about 4-10, and most preferably about 6-8 nt long and/or the overhang is about 1-20, and more preferably about 2-15 nt long. In certain aspects, the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may, but need not comprise a plurality of U residues, e.g., between 1 and 5 U residues. Classical siRNAs as described above trigger degradation of mRNAs to which they are targeted, thereby also reducing the rate of protein synthesis. In addition to siRNAs that act via the classical pathway, certain siRNAs that bind to the 3' UTR of a template transcript may inhibit expression of a protein encoded by the template transcript by a mechanism related to but distinct from classic RNA interference, e.g., by reducing translation of the transcript rather than decreasing its stability. Such RNAs are referred to as microRNAs (miRNAs) and are typically between approximately 20 and 26 nucleotides in length, e.g., 22 nt in length. It is believed that they are derived from larger precursors known as small temporal RNAs (stRNAs) or mRNA precursors, which are typically approximately 70 nt long with an approximately 4-15 nt loop. Endogenous RNAs of this type have been identified in a number of organisms including mammals, suggesting that this mechanism of post-transcriptional gene silencing may be widespread. MicroRNAs have been shown to block translation of target transcripts containing target sites.

siRNAs such as naturally occurring or artificial (i.e., designed by humans) mRNAs that bind within the 3' UTR (or elsewhere in a target transcript) and inhibit translation may tolerate a larger number of mismatches in the siRNA/template duplex, and particularly may tolerate mismatches within the central region of the duplex. In fact, there is evidence that some mismatches may be desirable or required as naturally occurring stRNAs frequently exhibit such mismatches as do mRNAs that have been shown to inhibit translation in vitro. For example, when hybridized with the target transcript such siRNAs frequently include two stretches of perfect complementarity separated by a region of mismatch. A variety of structures are possible. For example, the mRNA may include multiple areas of nonidentity (mismatch). The areas of nonidentity (mismatch) need not be symmetrical in the sense that both the target (e.g., thymine DNA glycosylase) and the mRNA include non-paired nucleotides. Typically the stretches of perfect complementarity are at least 5 nucleotides in length, e.g., 6, 7, or more nucleotides in length, while the regions of mismatch may be, for example, 1, 2, 3, or 4 nucleotides in length.

Hairpin structures designed to mimic siRNAs and mRNA precursors are processed intracellularly into molecules capable of reducing or inhibiting expression of target transcripts (e.g., thymine DNA glycosylase). These hairpin structures, which are based on classical siRNAs consisting of two RNA strands forming a 19 bp duplex structure are classified as class I or class II hairpins. Class I hairpins incorporate a loop at the 5' or 3' end of the antisense siRNA strand (i.e., the strand complementary to the target transcript whose inhibition is desired) but are otherwise identical to classical siRNAs. Class II hairpins resemble mRNA precursors in that they include a 19 nt duplex region and a loop at either the 3' or 5' end of the antisense strand of the duplex in addition to one or more nucleotide mismatches in the stem. These molecules are processed intracellularly into small RNA duplex structures capable of mediating silencing. They appear to exert their effects through degradation of the target mRNA rather than through translational repression as is thought to be the case for naturally occurring mRNAs and stRNAs.

Thus, a diverse set of RNA molecules containing duplex structures is able to mediate silencing through various mechanisms. Any such RNA, one portion of which binds to a target transcript (e.g., thymine DNA glycosylase) and reduces its expression, whether by triggering degradation, by inhibiting translation, or by other means, may be considered an siRNA, and any structure that generates such an siRNA (i.e., serves as a precursor to the RNA) is useful.

A further method of RNA interference is the use of short hairpin RNAs (shRNA). A plasmid containing a DNA sequence encoding for a particular desired siRNA sequence is delivered into a target cell via transfection or virally-mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA transfection as the former can lead to stable, long-term inhibition of protein expression. Inhibition of protein expression by transfected siRNAs is a transient phenomenon that does not occur for times periods longer than several days. In some cases, though, this may be preferable and desired. In cases where longer periods of protein inhibition are necessary, shRNA mediated inhibition is preferable. The use of shRNA is preferred for some aspects of the invention. Typically, siRNA-encoding vectors are constructs comprising a promoter, a sequence of the target gene to be silenced in the sense orientation, a spacer, the antisense of the target gene sequence, and a terminator.

Inhibition of the expression of thymine DNA glycosylase can also be effectuated by other means that are known and readily practiced in the art. For example, antisense nucleic acids can be used. Antisense RNA transcripts have a base sequence complementary to part or all of any other RNA transcript in the same cell. Such transcripts modulate gene expression through a variety of mechanisms including the modulation of RNA splicing, the modulation of RNA transport and the modulation of the translation of mRNA. Accordingly, in certain aspects, inhibition of the expression of thymine DNA glycosylase in a cell can be accomplished by expressing an antisense nucleic acid molecule in the cell.

Antisense nucleic acids are generally single-stranded nucleic acids (DNA, RNA, modified DNA, or modified RNA) complementary to a portion of a target nucleic acid (e.g., an mRNA transcript) and therefore able to bind to the target to form a duplex. Typically, they are oligonucleotides that range from 15 to 35 nucleotides in length but may range from 10 up to approximately 50 nucleotides in length. Binding typically reduces or inhibits the expression of the target nucleic acid, such as the gene encoding the target signal protein. For example, antisense oligonucleotides may block transcription when bound to genomic DNA, inhibit translation when bound to mRNA, and/or lead to degradation of the nucleic acid. Inhibition of the expression of thymine DNA glycosylase can be achieved by the administration of antisense nucleic acids comprising sequences complementary to those of the mRNA that encodes thymine DNA glycosylase.

Antisense oligonucleotides can be synthesized with a base sequence that is complementary to a portion of any RNA transcript in the cell. Antisense oligonucleotides can modulate gene expression through a variety of mechanisms including the modulation of RNA splicing, the modulation of RNA transport and the modulation of the translation of mRNA. Various properties of antisense oligonucleotides including stability, toxicity, tissue distribution, and cellular uptake and binding affinity may be altered through chemical modifications including (i) replacement of the phosphodiester backbone (e.g., peptide nucleic acid, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C).

Inhibition of thymine DNA glycosylase can also be effectuated by use of ribozymes. Certain nucleic acid molecules referred to as ribozymes or deoxyribozymes have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation.

In some aspects, the cells can be specifically transformed with transcription-silencing nucleic acids such as shRNA or siRNA, or can be transformed with vectors encoding such nucleic acids such that the cell expresses the inhibitory nucleic acid molecules. Transformation of the cells can be carried out according to any means suitable in the art.

A cell can be transformed with such nucleic acid molecules according to any means available in the art such as those describe or exemplified herein. It is preferred that cells are stably transformed with a vector comprising a nucleic acid sequence encoding such regulatory nucleic acid molecules, although transiently transformations are suitable. Any vector suitable for transformation of the particular cell of interest can be used. In preferred embodiments, the vector is a viral vector. In some embodiments, the viral vector is a lentivirus vector.

In some preferred aspects, the nucleic acid molecule is a siRNA that specifically hybridizes under stringent conditions to mRNA encoding thymine DNA glycosylase. In some preferred aspects, the nucleic acid molecule is a shRNA that specifically hybridizes under stringent conditions to mRNA encoding thymine DNA glycosylase. The shRNA may comprise the nucleic acid sequence of SEQ ID NO:1 or the nucleic acid sequence of SEQ ID NO:2.

The invention also features methods for treating tumors, including tumors that express thymine DNA glycosylase. The methods comprise inhibiting the expression or inhibiting the biologic activity of TDG in at least a cell of the tumor, preferably inhibiting the expression or the biologic activity of TDG in substantially all of the tumor cells, and inducing DNA damage in the cell. The tumor may be any tumor, particularly any tumor that expresses TDG. In preferred aspects, the tumor is a tumor of the pancreas, tumor of the lung, tumor of the head and neck, tumor of the hematopoietic system, tumor of the kidney, tumor of the breast, tumor of the ovary, tumor of the colon, tumor of the lymph nodes, tumor of the bladder, tumor of the prostate gland, tumor of the stomach, tumor of the skin (e.g., melanoma), or a tumor of the esophagus. The tumors may be treated in any subject, which may be a mammal such as a farm animal (e.g., horse, cow, sheep, pig), laboratory animal (e.g., mouse, rat, rabbit), companion animal (e.g., dog, cat), or non-human primate (e.g., new world monkey and old world monkey). In preferred aspects, the subject is a human being.

Inhibiting the expression of TDG may comprise transforming the cell with a nucleic acid molecule that interferes with the expression of thymine DNA glycosylase, including an RNA interference nucleic acid molecule. In some aspects, the nucleic acid molecule is a siRNA that specifically hybridizes under stringent conditions to mRNA encoding TDG. In some preferred aspects, the nucleic acid molecule is a shRNA that specifically hybridizes under stringent conditions to mRNA encoding thymine DNA glycosylase. The shRNA may comprise the nucleic acid sequence of SEQ ID NO:1 or the nucleic acid sequence of SEQ ID NO:2. Inhibiting the biologic activity of TDG may comprise contacting the cell with an effective amount of an agent that inhibits the biologic activity of TDG. Suitable agents include, for example, juglone, closantel, and cefixime, and pharmaceutically acceptable salts thereof. Such TDG-inhibiting agents may be used in combination with each other.

In any of the methods described herein, including methods for enhancing sensitivity and methods for treating, that comprise inducing DNA damage, DNA damage may be induced according to any suitable technique for inducing DNA damage. For example, inducing DNA damage in a tumor cell may comprise exposing the cell to an amount of radiation sufficient to induce DNA damage. The radiation may comprise ionizing radiation, may comprise x-radiation (x-ray), or may comprise gamma irradiation.

Inducing DNA damage in a tumor cell may comprise contacting the cell with an effective amount of an agent that damages DNA, or at least inhibits repair of DNA damage. The agent may comprise an antineoplastic alkylating agent, for example, a nitrogen mustard agent, chlorambucil, melphelan, or methyl methanesulfonate; a nitrosourea agent; an alkyl sulfonate agent; a triazine agent; or an ethylenimine agent. Bendamustine is a preferred example of an alkylating agent. The agent may comprise an antineoplastic intercalating agent, for example, a platinum agent such as cisplatin, cisplatinin, or oxaliplatin. The agent may comprise a topoisomerase I inhibitor or a topoisomerase II inhibitor. The agent may comprise a pyrimidine analog, for example, a fluoruracil or gemcitabine.

The invention also features methods for treating malignancies in a subject in need thereof. The malignancy may be any malignancy in which TDG is expressed, including but not limited to a malignancy of the pancreas, a malignancy of the head and neck, a malignancy of the lung, a malignancy of the hematopoietic system, a malignancy of the kidney, a malignancy of the bladder, a malignancy of the prostate gland, a malignancy of the colon, a malignancy of the breast, a malignancy of the ovary, a malignancy of the lymph nodes, a malignancy of the stomach, a malignancy of the skin (e.g., melanoma), or a malignancy of the esophagus. The malignancy may be a malignancy that is not sensitive to low doses of gemcitabine or bendamustine in the absence of the inhibition of the expression or the biologic activity of TDG. The subject may be a mammal such as a farm animal (e.g., horse, cow, sheep, pig), laboratory animal (e.g., mouse, rat, rabbit), companion animal (e.g., dog, cat), or non-human primate (e.g., new world monkey and old world monkey). In preferred aspects, the subject is a human being.

In general, a method for treating a malignancy of the pancreas, lung, head and neck, hematopoietic system, kidney, bladder, prostate gland, colon, breast, ovary, lymph nodes, skin, stomach, or esophagus, among others, comprises administering to the malignancy in a subject in need thereof an effective amount of an agent that inhibits the expression or inhibits the biologic activity of TDG, and inducing DNA damage in the malignancy. The agent may be administered systemically, or may be administered proximally or locally to the malignancy itself. The agent may comprise cefixime, juglone, closantel, or a pharmaceutically acceptable salt thereof, or any combination thereof. Inhibiting the expression of TDG may comprise transforming a cell in the malignancy with a nucleic acid molecule that interferes with the expression of thymine DNA glycosylase, including an RNA interference nucleic acid molecule. In some aspects, the nucleic acid molecule is a siRNA that specifically hybridizes under stringent conditions to mRNA encoding TDG. In some preferred aspects, the nucleic acid molecule is a shRNA that specifically hybridizes under stringent conditions to mRNA encoding thymine DNA glycosylase. The shRNA may comprise the nucleic acid sequence of SEQ ID NO:1 or the nucleic acid sequence of SEQ ID NO:2.

Inducing DNA damage in the malignancy may comprise administering to the malignancy an effective amount of an agent that damages DNA, or at least inhibits repair of DNA damage. The agent may comprise an antineoplastic alkylating agent, for example, a nitrogen mustard agent, a nitrosourea agent, an alkyl sulfonate agent, a triazine agent, or an ethylenimine agent. Bendamustine is a preferred example of an alkylating agent. The agent may comprise an antineoplastic intercalating agent, for example, a platinum agent such as cisplatin. The agent may comprise a topoisomerase I inhibitor or a topoisomerase II inhibitor. The agent may comprise a pyrimidine analog, for example, a fluoruracil or gemcitabine. DNA damage may be induced by exposing the malignancy to an amount of radiation sufficient to induce DNA damage in a cell of the malignancy. The radiation may comprise ionizing radiation. The agent may be administered systemically, or may be administered proximally or locally to the malignancy itself.

In some detailed aspects, treatment may comprise administering to a subject in need thereof an amount of juglone effective to inhibit TDG in the subject, and an amount of bendamustine or gemcitabine effective to induce DNA damage in the subject such that a malignancy of the pancreas, lung, head and neck, hematopoietic system, kidney, bladder, prostate gland, colon, breast, ovary, lymph nodes, skin, stomach, or esophagus is treated in the subject. In some aspects, treatment may comprise administering to a subject in need thereof an amount of closantel effective to inhibit TDG in the subject, and an amount of bendamustine or gemcitabine effective to induce DNA damage in the subject such that a malignancy of the pancreas, lung, head and neck, hematopoietic system, kidney, bladder, prostate gland, colon, breast, ovary, lymph nodes, skin, stomach, or esophagus is treated in the subject. In some aspects, treatment may comprise administering to a subject in need thereof an amount of cefixime effective to inhibit TDG in the subject, and an amount of bendamustine or gemcitabine effective to induce DNA damage in the subject such that a malignancy of the pancreas, lung, head and neck, hematopoietic system, kidney, bladder, prostate gland, colon, breast, ovary, lymph nodes, skin, stomach, or esophagus is treated in the subject.

The invention also features methods for screening compounds that synergize with TDG inhibition. In some aspects, a screening method comprises contacting a tumor cell in which the expression or the biologic activity of TDG has been inhibited with a test compound, in parallel, contacting the same type of tumor cell in which the expression or the biologic activity of TDG has not been inhibited with the test compound. A sufficient period of time following contacting of the cells with the test compound, the method comprises measuring the level of cytotoxicity of cells in which TDG has been inhibited relative to the level of cytotoxicity of cells in which TDG has not been inhibited. A higher level of cytotoxicity in cells in which TDG has been inhibited may indicate that cytotoxicity of the test compound is TDG-dependent. A screening method may further comprise determining if the test compound induces DNA damage.

The tumor cells used in the method may comprise tumor cells of the pancreas, tumor cells of the head and neck, tumor cells of the hematopoietic system, tumor cells of the lung, tumor cells of the kidney, tumor cells of the breast, tumor cells of the ovary, tumor cells of the ovary, tumor cells of the lymph nodes, tumor cells of the bladder, tumor cells of the prostate gland, tumor cells of the stomach, tumor cells of the skin (e.g., melanoma cells) or tumor cells of the esophagus, among others. Expression of TDG may be inhibited with a nucleic acid molecule that interferes with the expression of TDG, for example, a siRNA that specifically hybridizes under stringent conditions to mRNA encoding thymine DNA glycosylase or a shRNA that specifically hybridizes under stringent conditions to mRNA encoding thymine DNA glycosylase. A shRNA may comprise the nucleic acid sequence of SEQ ID NO:1 or the nucleic acid sequence of SEQ ID NO:2.

In parallel, a tumor cell in which the expression of TDG has been inhibited may be contacted with an agent that is known to cause cytotoxicity by synergizing with TDG inhibition, in order to serve as a positive control or as a reference value, and another tumor cell may be contacted with an agent that is known not to cause cytotoxicity by synergizing with TDG inhibition in order to serve as a negative control.

The test compound may be contacted with the tumor cells before inhibiting the expression or biologic activity of TDG in the cells, substantially at the same time as inhibiting the expression or biologic activity of TDG in the cells, or after inhibiting the expression or biologic activity of TDG in the cells. The period of time before or after contacting cells with the CYP1B1 activator may vary, and may be any suitable period of time, e.g., seconds, minutes, hours, or days.

Cytotoxicity may be measured according to any technique suitable in the art, including commercially available kits and assays, fluorescence or light microscopy, flow cytometry, acridine orange/ethidium bromide staining, and other suitable techniques. Preferably, the measurements are quantitative. Commercially available kits include cell viability assays such as Cell Titer-Glo®, Cell Titer-Blue®, and apoptosis assay such as Guava Nexin®. Standard clonogenic assay that count surviving colonies at a defined time point after drug treatment may also be used The invention also features kits. The kits may be used, for example, to practice any of the methods described or exemplified herein. In some aspects, a kit comprises a nucleic acid molecule that interferes with the expression of thymine DNA glycosylase, a composition comprising gemcitabine and a pharmaceutically acceptable carrier, and instructions for using the kit in a method for enhancing the sensitivity of a tumor cell to gemcitabine, or instructions for using the kit in a method for treating a tumor, or a method for treating a malignancy. The nucleic acid molecule may be a siRNA and/or a shRNA that specifically hybridizes under stringent conditions to mRNA encoding thymine DNA glycosylase. The shRNA may comprise the nucleic acid sequence of SEQ ID NO:1 or the nucleic acid sequence of SEQ ID NO:2. The tumor cell, tumor, or malignancy may be one of the pancreas, lung, head and neck, kidney, hematopoietic system, breast, ovary, colon, lymph nodes, bladder, prostate gland, skin (e.g., melanoma) stomach, or esophagus.

In some aspects, a kit comprises a nucleic acid molecule that interferes with the expression of thymine DNA glycosylase, a composition comprising bendamustine and a pharmaceutically acceptable carrier, and instructions for using the kit in a method for enhancing the sensitivity of a tumor cell to gemcitabine, or instructions for using the kit in a method for treating a tumor, or a method for treating a malignancy. The nucleic acid molecule may be a siRNA and/or a shRNA that specifically hybridizes under stringent conditions to mRNA encoding thymine DNA glycosylase. The shRNA may comprise the nucleic acid sequence of SEQ ID NO:1 or the nucleic acid sequence of SEQ ID NO:2. The tumor cell, tumor, or malignancy may be one of the pancreas, lung, head and neck, kidney, hematopoietic system, breast, ovary, lymph nodes, colon, bladder, prostate gland, skin (e.g., melanoma) stomach, or esophagus.

In some aspects, a kit comprises a composition comprising juglone and a pharmaceutically acceptable carrier, and a composition comprising gemcitabine and a pharmaceutically acceptable carrier or bendamustine and a pharmaceutically acceptable carrier, and instructions for using the kit in a method for enhancing the sensitivity of a tumor cell to gemcitabine or to bendamustine, or instructions for using the kit in a method for treating a tumor, or a method for treating a malignancy. The tumor cell, tumor, or malignancy may be one of the pancreas, lung, head and neck, kidney, hematopoietic system, breast, ovary, lymph nodes, colon, bladder, prostate gland, skin (e.g., melanoma) stomach, or esophagus.

In some aspects, a kit comprises a composition comprising closantel and a pharmaceutically acceptable carrier, and a composition comprising gemcitabine and a pharmaceutically acceptable carrier or bendamustine and a pharmaceutically acceptable carrier, and instructions for using the kit in a method for enhancing the sensitivity of a tumor cell to gemcitabine or to bendamustine, or instructions for using the kit in a method for treating a tumor, or a method for treating a malignancy. The tumor cell, tumor, or malignancy may be one of the pancreas, lung, head and neck, kidney, hematopoietic system, breast, ovary, lymph nodes, colon, bladder, prostate gland, skin (e.g., melanoma) stomach, or esophagus.

In some aspects, a kit comprises a composition comprising cefixime and a pharmaceutically acceptable carrier, and a composition comprising gemcitabine and a pharmaceutically acceptable carrier or bendamustine and a pharmaceutically acceptable carrier, and instructions for using the kit in a method for enhancing the sensitivity of a tumor cell to gemcitabine or to bendamustine, or instructions for using the kit in a method for treating a tumor, or a method for treating a malignancy. The tumor cell, tumor, or malignancy may be one of the pancreas, lung, head and neck, kidney, hematopoietic system, breast, ovary, lymph nodes, colon, bladder, prostate gland, skin (e.g., melanoma) stomach, or esophagus.

The following examples are provided to describe the invention in greater detail. They are intended to illustrate, not to limit, the invention.

Example 1

Materials and Methods

Materials. Gemcitabine was obtained from an in-house pharmacy, and bendamustine, propidium iodide, chlorambucil, melphalan and Chk2 inhibitor II were all purchased from Sigma Chemical Company. The UCN-01 was generously provided by Kyowa Hakko Kirin Co., Ltd. and the National Cancer Institute, NIH.

Cell lines and culture conditions. All cell lines were originally obtained from the ATCC and banked at an in-house cell culture facility. Mycoplasma testing was conducted prior to studies. The cell lines Hela, PANC1, BxPC3, MCF7, MDA-MB-453 were grown in DMEM supplemented with 10% FBS, 2 mM glutamine and 1% penicillin, streptomycin and kanamycin (PSK). OVCAR 5 and 10 cells were grown in RPMI supplemented with 10% FBS, 2 mM glutamine and 1% PSK. U2932 cells were grown in RPMI supplemented with 15% FBS, 2 mM glutamine and 1% PSK. Wildtype and TDG$^{-/-}$ mouse embryo fibroblasts (MEFs) generated previously were grown in DMEM supplemented with 15% FBS, 2 mM glutamine, 1% PSK and sodium pyruvate. All cells were maintained at 37° C., 5% $CO_2$.

Cell viability and apoptosis assays. Hela cells were seeded into 96 well plates at a density of 1500 cells per well. Cells were treated with BDM (3.125-200 µM) for 24 h. After this time cells were additionally treated either with UCN-01 (100 nM), Chk2 inhibitor (100 nM) or Gö6976 (200 nM) for an additional 24 h. MTS reagent (CellTiter 96® AQueous Proliferation Assay, Promega) was added to each well for 4 h before the absorbance values at 490 nm was read. Experiments were conducted in triplicate, 3 independent times. Data presented are the average absorbance values, relative to control±SD. For apoptosis determination, cells seeded and treated as stated above were stained with Guava Nexin Reagent® (Millipore). Analysis was conducted using the Easycyte module and Cytosoft Software® (Millipore). Experiments were conducted 3 independent times, collecting 2000 events each time. Data shown is the average±SD.

Clonogenic assay. Hela cells were seeded into 6 well plates at a density of 1000 cells per well. Cells were treated for 24 h. Cells were then treated with and without UCN-01 (100 nM) for 3 h. All drugs were washed out and cells were left to grow for approximately 10 days. Cells were fixed using Acetic acid:methanol:$H_2O$, (10:10:80), dried and stained with 0.4% crystal violet in 20% ethanol. Qualitative images of representative results are presented. For quantification, colonies were solubilized (1% acetic acid, 30% ethanol) and absorbance values at 595 nm were read. Values are expressed as a percentage relative to untreated cells, with untreated cells set to 100%±SD. Experiments were conducted in triplicate, three independent times. Student's two-tailed unpaired t test was conducted for statistics.

Metaphase spreads. Mitotic cells were collected from untreated and bendamustine at 50 µM or 200 µM+UCN-01 (100 nM) treatments. For visualizing, cells were dropped onto a glass slides and stained with DAPI. Mitotic spreads were viewed and imaged using fluorescence microscopy. Images shown are representative of those observed.

Electron microscopy. Hela cells were seeded into 6 cm dishes, synchronized with thymidine (2 mM) and treated with BDM 50 µM, 200 µM or gemcitabine (100 µM) for 18 h. Cells treated with UCN-01 (100 µM) for an addition 9 h to obtain mitotic cells were fixed with glutaraldehyde solution (3%, pH 7.4). Samples were prepared for electron microscopy analysis.

Immunofluorescence. Cells were grown on coverslips, treated with the indicated drugs, fixed and stained. To detect DNA damage induction and repair, antibodies against 53BP1 (Bethyl) and γ-H2AX (Upstate) were used with Alexa Fluor-conjugated secondary antibodies (Invitrogen). All cells were counter-stained with DAPI (Molecular probes). Images were captured using a 40× or 100× objective mounted on an inverted microscope (Eclipse TE2000S; Nikon) with a CCD camera (Photometrics Cascade 512F; Roper Scientific) powered by NIS Elements AR (version 3.10) software (Nikon). For quantitative analysis, individual nuclei were identified using DAPI staining and used to define region of interests (ROI), which were then transposed onto other channels. The sum intensity per nuclei from a minimum of 50 nuclei was averaged±SEM.

EdU incorporation. Hela cells were treated with nocodazole for 14 h after which time mitotic cells were collected by mechanical shake-off. Cells were washed twice with medium and re-plated. BDM and EdU (10 µM) (Click-IT™ EdU imaging kit, Invitrogen) were added 2 h later, when the cells were fully adherent and still in G1, and incubated for an additional 12 h. Cells were fixed and stained according to the manufacturer's protocol. Quantification of EdU incorporation was performed as described for antibody detection.

Time-lapse video microscopy. Hela cells stably expressing GFP:histone H2B were seeded into 6 well plates and synchronized in S phase using thymidine (2 mM). Thymidine was washed out and 11 h later cells were treated with the indicated drugs for an additional 18 h. Where appropriate, UCN-01 (100 nM) was added to wells before being supplemented with HEPES (25 mM), layered with mineral oil (Sigma) and placed into a housing chamber which maintained the temperature at 37° C. Using a Nikon TE2000 microscope (Nikon) controlled by MetaMorph software (Molecular Devices), brightfield and fluorescent images were captured every 5 minutes for up to 48 h. Individual movies were analyzed manually and a minimum of 100 cells per treatment scored for the indicated measurements. For montages, selected frames representing different cell morphologies are presented.

DNA content analysis via flow cytometry. Following indicated drug treatments, cells were fixed with 70% ethanol. For analysis, cells were stained with propidium iodide, RNase A and sodium citrate. Cells were incubated at 37° C. for 30 minutes before being analyzed using a Becton Dickinson single laser three-fluorescence FACScan flow analyzer and Cell Quest software (Becton Dickinson). DNA content was acquired from 10,000 events and FlowJo software was used to process the data.

Statistical analysis. For statistical analyses, Student's two-tailed t test was conducted.

Example 2

Bendamustine Displays Concentration-Dependent Effects on Cell Cycle Response

Figure 1B:
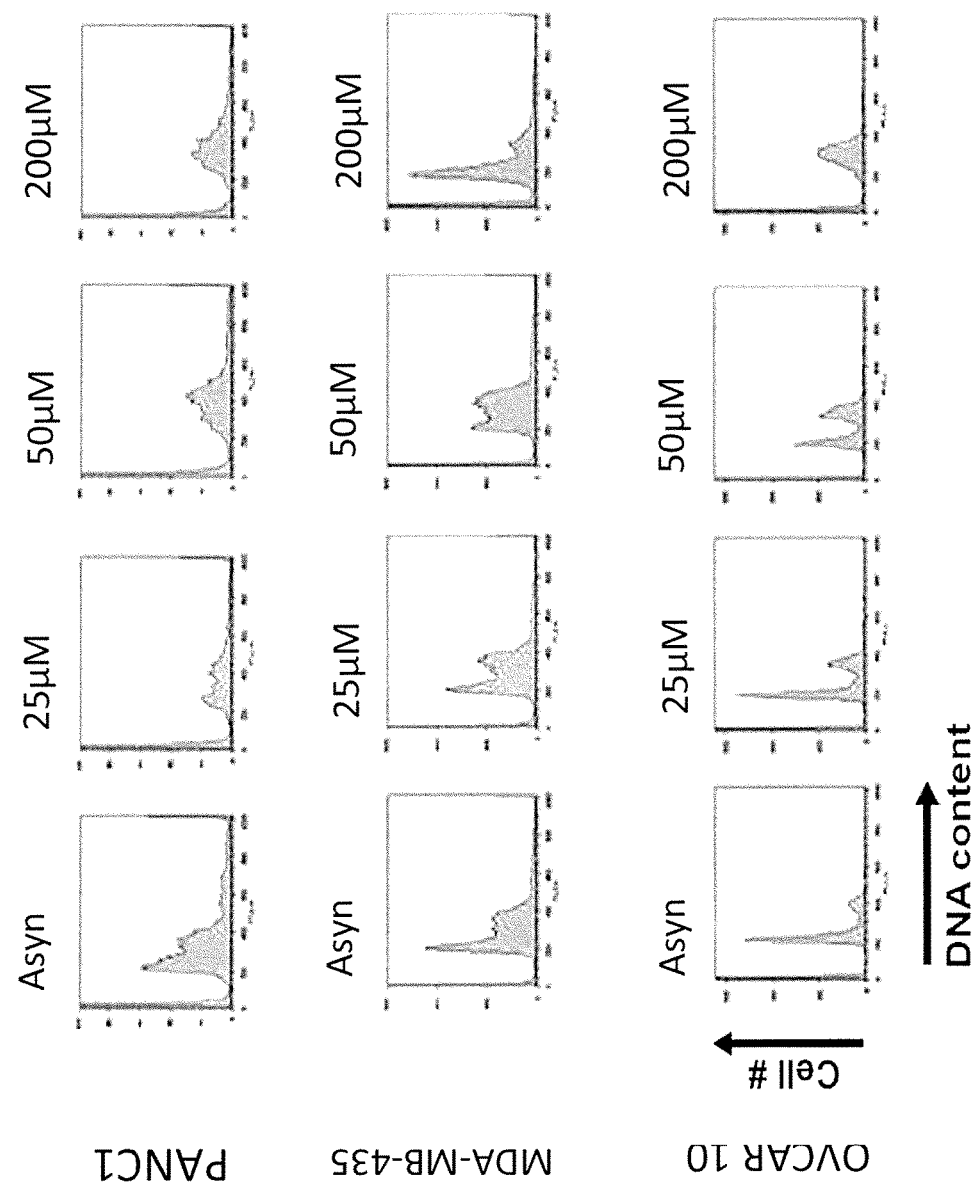

Hela cells synchronized in G1 bp release from a mitotic shakeoff were treated with increasing concentrations of bendamustine (BDM), and their cell cycle profiles were assessed 24 h later. FIG. 1 shows that cells treated with increasing doses of BDM (25-100 µM) accumulated as 4N DNA content indicating a G2/M delay. In contrast, cells treated with 200 µM BDM were arrested in S phase. The dose dependent effects of BDM on the cell cycle were next assessed in a wide panel of cancer cell lines. Cell lines derived from pancreatic (PANC1 and BXPC3 cells), breast (MCF-7 and MDA-MB-435), and ovarian (OVCAR 5 and 10) cancers responded similarly to Hela cells (FIG. 1A and FIG. 1B). 50 µM BDM caused a G2 arrest while 200 µM BDM resulted in an S phase arrest. The concentrations of BDM used here are consistent with those previously used against a number of epithelial derived cell lines, but are generally higher than concentrations used for leukemic cell lines. To test if this was a feature of adherent cell lines, the U2932 B cell lymphoma cells were treated with BDM. As seen with the adherent cell lines, U2932 cells also exhibited a dose dependent cell cycle response, but at a lower concentration: 10 µM induced a G2 arrest, 50 µM induced an S phase arrest. The combined data demonstrate that BDM induces a dose-dependent effect on cell cycle progression in multiple cell lines.

DNA synthesis was measured to further assess the effects of BDM on cell cycle progression. Hela cells synchronized by mitotic shake-off were treated in G1 with either 50 or 200 µM BDM in the presence of EdU (10 µM) for 12 h. Cells treated with 50 µM BDM incorporated the same amount of EdU as untreated cells (untreated set to 100±4.8% versus BDM 50 µM 98.0±4.1%), while cells treated with 200 µM BDM incorporated only 64.7±2.6% as compared to the control (P<STATS). This suggests that 200 µM BDM reduces the efficiency of replication, that delays S phase progression. Although replication was not grossly affected by 50 µM BDM, the G2 delay may reflect accumulation of replication errors that did escape the S phase checkpoint.

Example 3

Bendamustine Induces Both Repairable and Irreparable DNA Damage

The cell cycle arrest (FIG. 1) induced by bendamustine suggested BDM that induced DNA damage, thereby activating the DNA damage checkpoint pathway. Therefore, phospho-H2AX (Ser 139), 53BP1 and RPA, three distinct proteins intimately involved in the DNA damage response, were evaluated as a direct measure of BDM-induced DNA damage. It was observed that 53BP1, RPA, and γ-H2AX nuclear foci, which reflect accumulation at sites of DNA damage, were all increased in a dose-dependent manner.

Figure 2A:
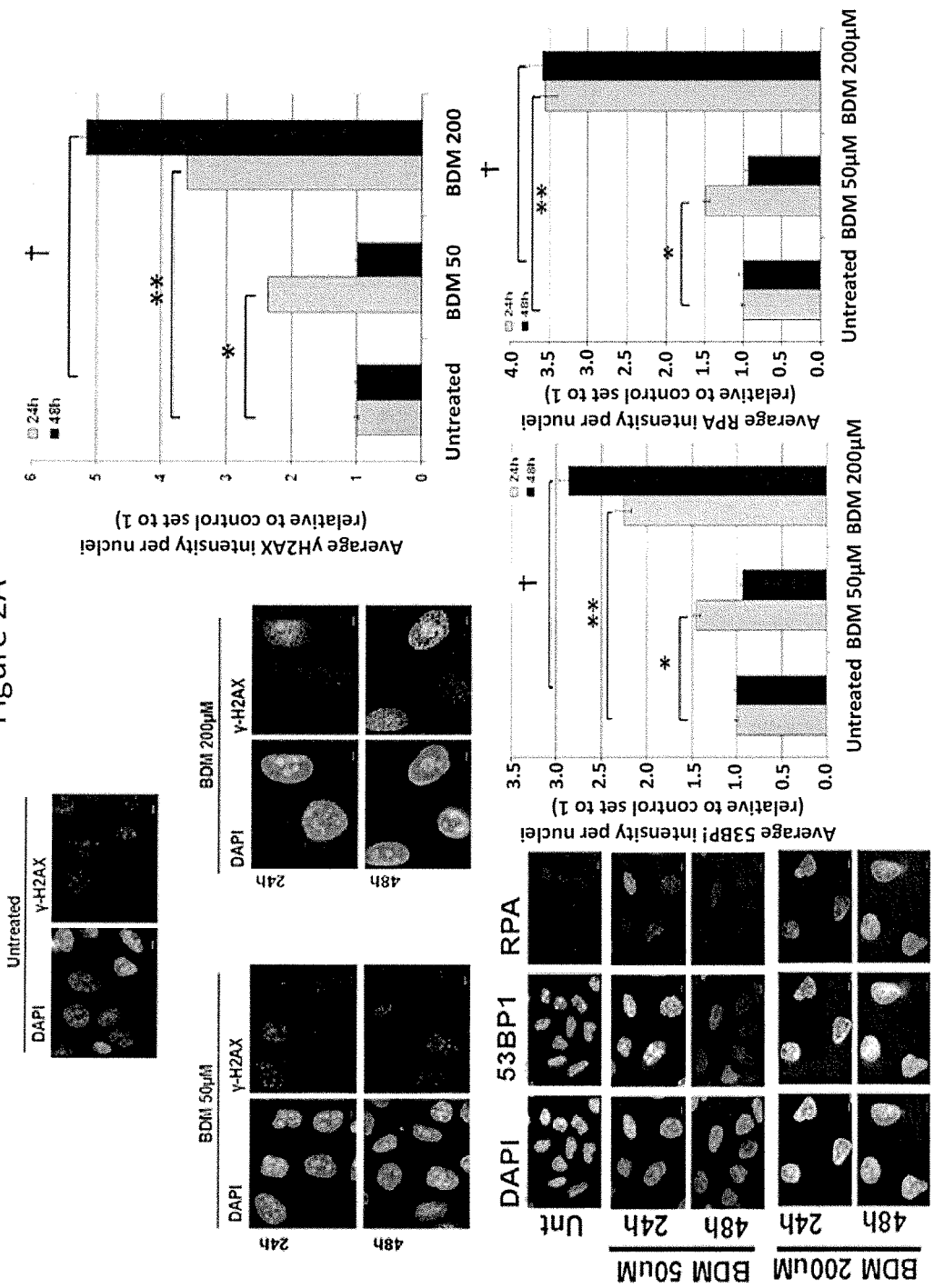
FIGS. 2A-2C show that bendamustine induces both repairable and irreparable DNA damage. Hela cells were treated for 24 or 48 h continuous treatment or of either 50 or 200 µM BDM or 24 h followed by 24 h in the absence of drugs.

Next, the efficiency of repair of the damaged DNA induced by 50 µM BDM and 200 µM was assessed by monitoring the loss of the DNA damage foci. Cells treated with BDM 50 µM for 24 h accumulated γ-H2AX, RPA and 53BP1 foci. These foci were reduced to levels comparable to untreated cells at 24 h after washout of BDM. Even when cells were continuously exposed to 50 µM BDM for 48 h, γ-H2AX, RPA and 53BP1 staining was also reduced to control cells (FIG. 2A and data not shown). When cells were treated with BDM at 200 µM for 24 h, an increase in γ-H2AX, RPA and 53BP1 was also observed. However, unlike cells treated with 50 µM BDM, foci persisted after drug was removed. Furthermore, the DNA damage was not reduced after 48 h of continuous exposure to BDM at 200 µM.

Analysis of Chk1 phosphorylation (Ser-345), a key regulator of cell cycle control in response to DNA damage, corroborated the immunofluorescence findings. Chk1 was dose-dependently phosphorylated by BDM after 24 h treatment. However, after 48 h, no signal was observed in cells treated with 50 µM BDM, but detectable pChk1 was still present in cells treated with 200 µM BDM.

Figure 2C:
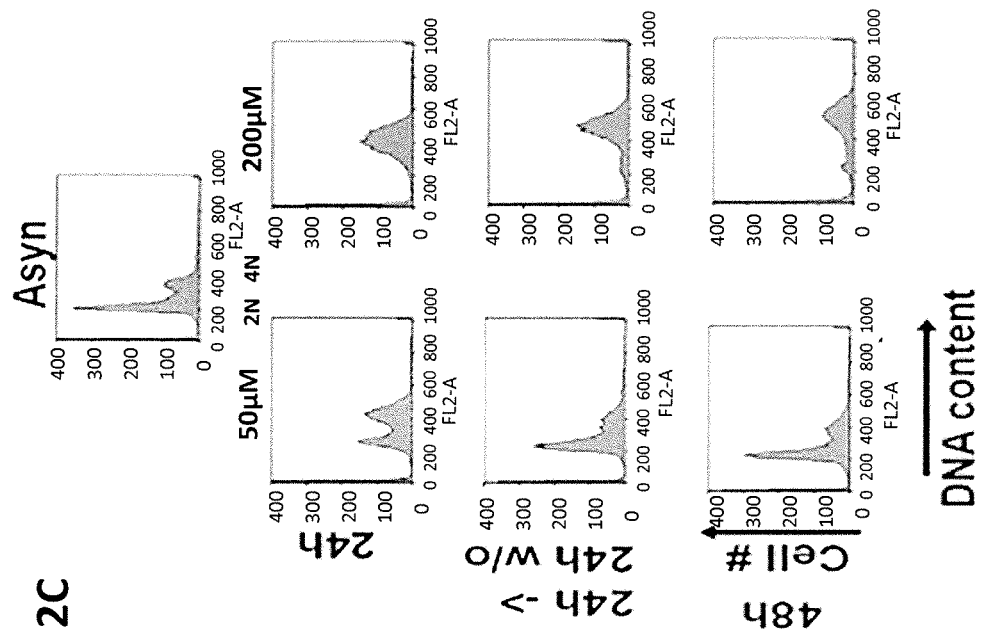
Figure 2B:
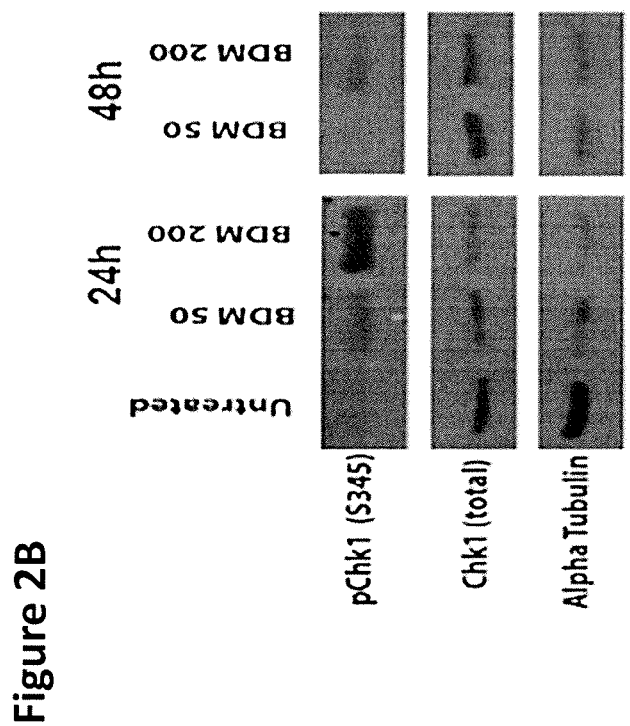

To assess whether the transient or sustained DNA damage correlated with cell cycle progression, cell cycle profiles were measured after cells were treated with BDM at 50 and 200 µM for 24 h, 48 h continuously or for 24 h with BDM, followed by 24 h in the absence of drug. FIG. 2C shows the expected cell cycle arrest after treatment with 50 µM BDM for 24 h, but after another 24 h in the presence or absence of BDM, cells displayed a normal cell cycle profile. In contrast, the cell cycle arrest induced by 200 µM BDM was maintained after drug washout, or 48 h continuous treatment. Taken together, these data suggest that DNA damage induced by 50 µM BDM is efficiently repaired, but at 200 µM BDM the effects on cell cycle and DNA damage were irreversible.

Example 4

Bendamustine-Induced DNA Damage Activates Base Excision Repair

Figure 3A:
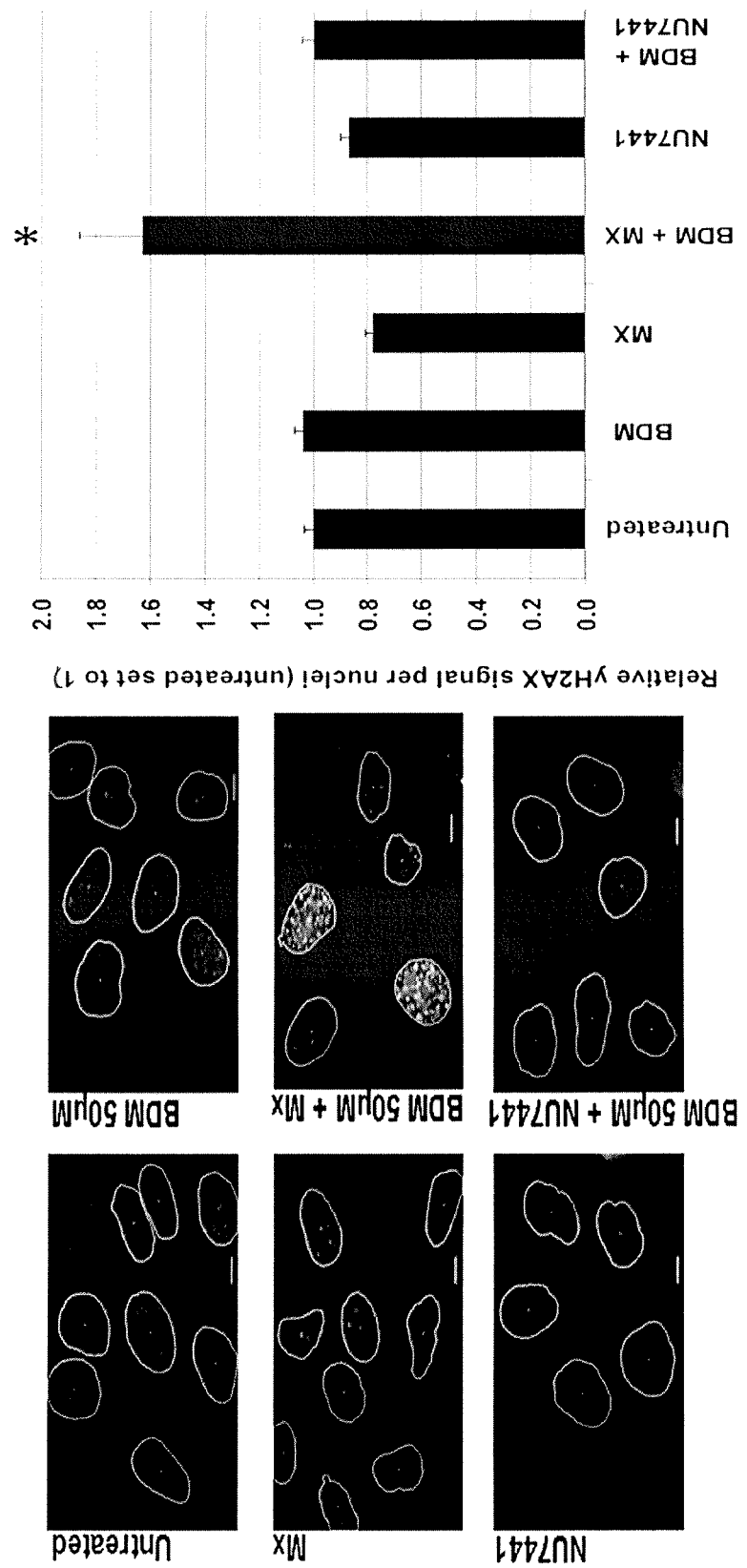

A previous study showed that BDM-induced cell death was enhanced by an inhibitor of base excision repair (BER) (Leoni L M et al. (2008) Clin. Cancer Res. 14:309-17). Therefore, whether BDM-induced damage is dependent upon BER was assessed in two ways. First, the essential BER protein apurinic/apyrimidinic endonuclease (APE1) was targeted using the pharmacological inhibitor methoxyamine (MX). Hela cells were treated with BDM 50 µM in the presence and absence of methoxyamine, and assessed DNA repair. Notably, the combination of MX and BDM resulted in significantly higher levels of γ-H2AX foci than BDM alone (FIG. 3A). In contrast, using NU7441, a DNA-PK inhibitor that does not inhibit BER, did not block repair of BDM-induced damage.

Second, mouse embryonic fibroblasts (MEFs) that were deficient in BER due to genetic ablation of thymine DNA glycosylase (TDG$^{-/-}$) were used. It was not only observed that TDG$^{-/-}$ MEFs were more sensitive to 10 µM BDM than wildtype MEFs, showing increased γ-H2AX staining after 24 h of treatment, but also that they had a reduced ability to repair the DNA damage after 48 h continuous treatment as compared to wildtype MEFs (FIG. 3B).

Example 5

Chk1 Inhibition Accelerates Bendamustine-Induced Cell Death

Figure 4A:
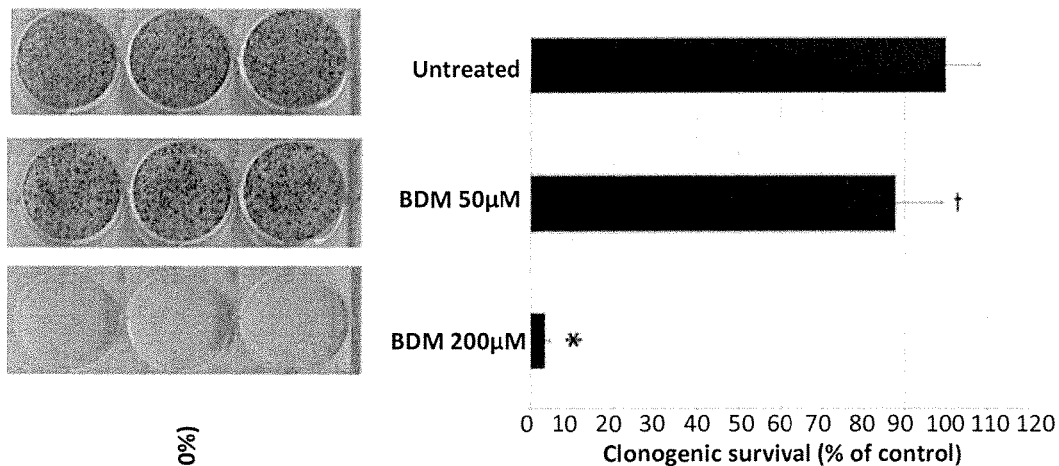
FIGS. 4A-4C show Chk1 inhibition accelerates bendamustine-induced cell death.

Since recent pharmacokinetic studies demonstrated that BDM is rapidly metabolized in patients, the clonogenic assay was modified to assess how transient exposure to BDM affects long term survival. Hela cells were treated for 24 h with BDM at 50 µM and 200 µM after which time drugs were washed out, replaced with fresh medium and allowed to recover. As shown in FIG. 4A, colony formation between control cells versus cells treated with 50 µM BDM was marginally reduced (control 100±8.1% versus 87.8±11.2%; p<0.05). However, cells treated with BDM 200 µM caused a dramatic reduction in the number of colonies formed (control 100±8.1% versus 3.5±1.3%; p<0.0001). Thus, concentrations of BDM (200 µM) that induced irreparable DNA damage and a sustained cell cycle arrest leads to efficient cell death. However, given the timescale reflected in the clonogenic assay after treatment with BDM 200 µM (~10 days), it is possible that cells may acquire resistance to the drug and escape.

Figure 4B:
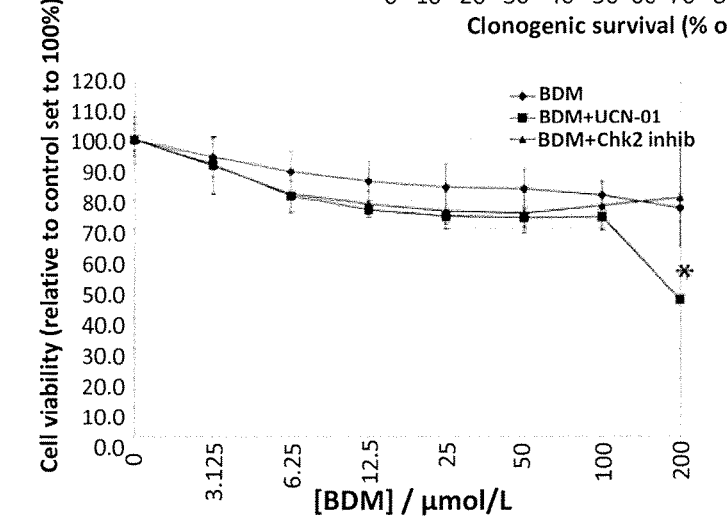

Since BDM 200 µM induced a sustained cell cycle arrest, it was hypothesized that abrogating the checkpoint would accelerate killing by BDM. FIG. 4B shows that bendamustine at any concentration (3.125-200 µM) is not particularly effective at killing Hela cells after 48 h of continuous treatment.

Next, cells were treated successively with BDM (3.125-200 µM) for 24 hours and then UCN-01 (100 nM) was added for another 24 h, before assaying for cell viability. UCN-01 did not sensitize cells pre-treated with BDM up to 100 µM to killing. In contrast, viability was significantly reduced in cells pre-treated with 200 µM BDM followed by UCN-01. Similar sensitization was observed with Gö6976, another compound that inhibits Chk1 (data not shown). A pharmacological inhibitor of Chk2 did not sensitize to killing by any concentration of BDM.

Figure 4C:
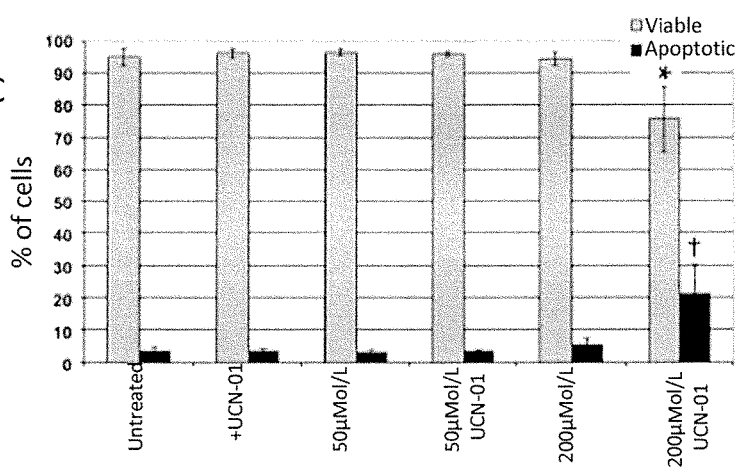

Having demonstrated Hela cell death was increased after BDM 200 µM+UCN-01, but not BDM 50 µM+UCN-01, the nature of killing was next examined. Cells were stained to discriminate between necrotic or apoptotic cell death. Notably, only cells treated with BDM 200 µM+UCN-01 and Gö6976 exhibited an increase in the percentage of apoptotic cells (p<0.01 vs. control) (FIG. 4C and data not shown). It should be noted that UCN-01 alone had no discernable effects on cell viability in any of the assays performed. Taken together, these findings demonstrate that forcing cells to overcome the checkpoint induced by 200 µM BDM, but not 50 µM, BDM causes cells to die more effectively than compared to cells treated with BDM alone.

Example 6

Figure 5A:
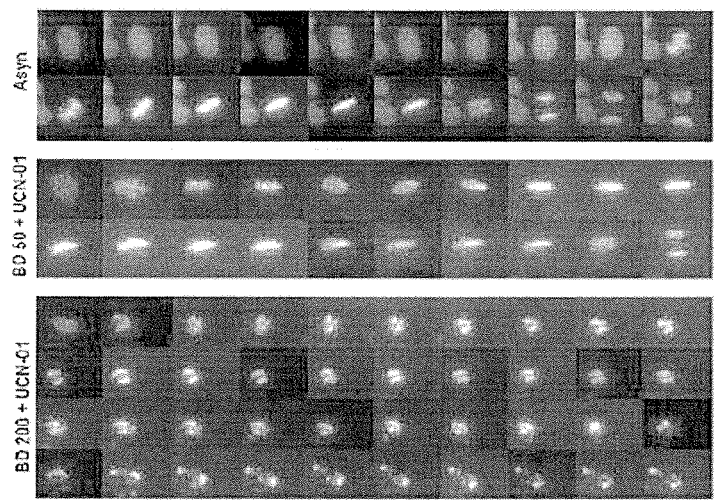
FIGS. 5A-5D show that overcoming bendamustine-induced checkpoint arrest via Chk1 inhibition forces cells into premature mitosis. Hela cells stably expressing GFP:histone H2B were used for live cell video-microscopy.

Overcoming Bendamustine-Induced Checkpoint Arrest Via Chk1 Inhibition Forces Cells into Premature Mitosis To gain insight as to how inhibition of Chk1 accelerated cells to killing by 200 µM BDM, the fates of individual cells were tracked by time-lapse microscopy. Hela cells stably expressing GFP:Histone H2B were treated with vehicle, 50 µM or 200 µM of BDM for 24 h before UCN-01 (100 nM) was added. The time-lapse data showed that vehicle treated cells treated entered and progressed normally through mitosis (average time of mitosis=52.5±16.7 minutes) (FIG. 5A, upper panel and FIG. 5D).

50 µM BDM caused a reduction in the percentage of cells entering mitosis over a 24 h period (FIG. 5D), consistent with the G2 arrest observed by FACs analysis. Addition of UCN-01 abrogated the arrest and cells began to enter mitosis 4 hours later (FIG. 5A, middle panel). While chromosome congression and alignment appeared normal, cells were nevertheless delayed at metaphase for an average 89±64.7 minutes, as compared to controls that exited 37.5±16.7 minutes after metaphase alignment.

Figure 5B:
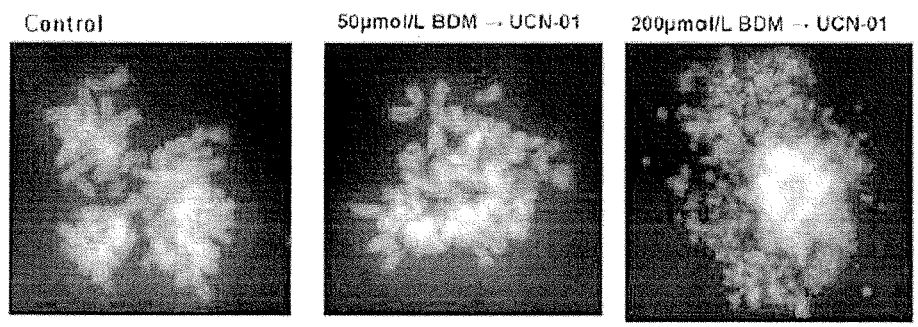
Figure 5C:
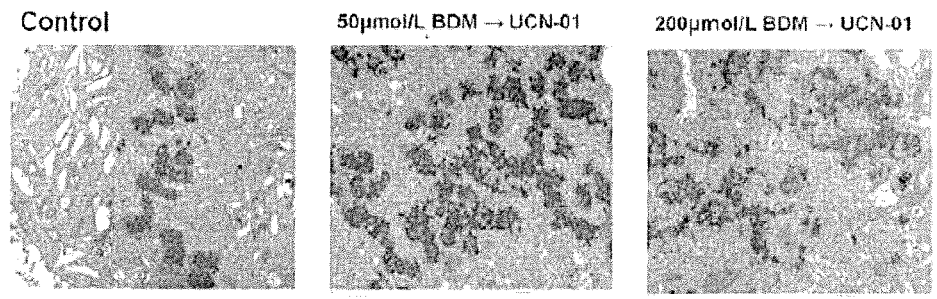
Figure 5D:
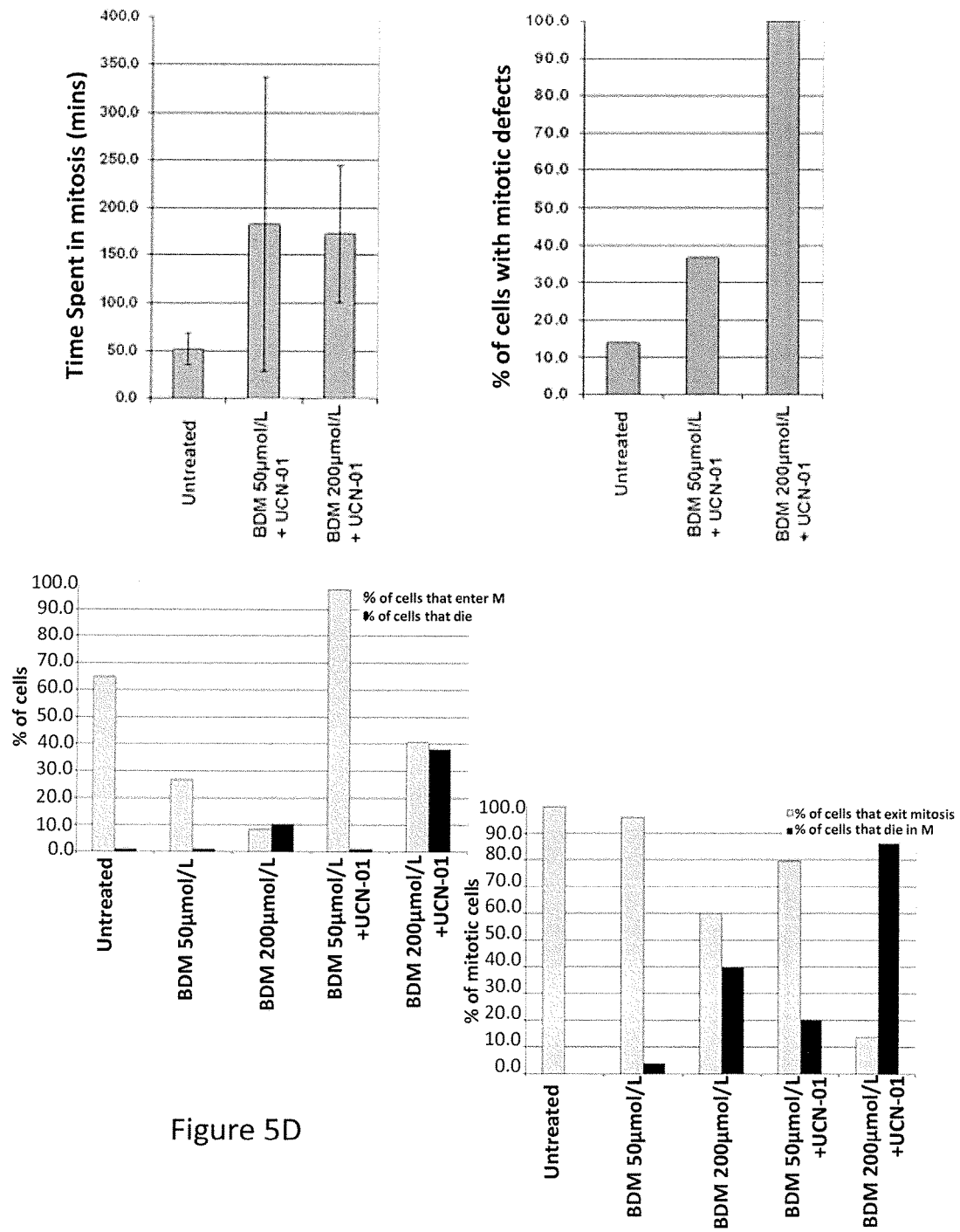

Upon exiting mitosis, a fraction exhibited chromosomal aberrations, such as lagging chromosomes (FIG. 5D). Similarly, cells treated with 200 µM BDM had a reduced mitotic index, consistent with the cell cycle data. Inhibition of Chk1 induced mitotic entry but, unlike at 50 µM BDM, the mitotic figures of these cells were highly abnormal (FIG. 5A, bottom panel). For example, the chromosomes failed to align at the spindle equator, and cells rarely exited mitosis but instead died without exiting. The few cells that did exit formed multinucleated cells. Thus, cells forced into mitosis after 50 µM BDM+Chk1 inhibition progress through mitosis relatively normally. In contrast, cells forced into mitosis after 200 µM BDM+Chk1 inhibition generate extremely abnormal mitotic figures, with the majority failing to exit and instead die in mitosis (FIG. 5D).

The chromosome morphology of cells that were forced to enter mitosis after treatment with 50 µM or 200 µM BDM+ UCN-01 was next evaluated in greater detail. Metaphase spreads obtained from control and BDM 50 µM+UCN-01 treated cells showed no obvious gross structural defects (FIG. 5B). In contrast, the metaphase spreads of BDM 200 µM+UCN-01 samples were extremely abnormal. Instead of forming discrete chromosomes, they appeared 'pulverized', a phenotype indicative of extensive chromosome fragmentation.

This is consistent with early studies that showed that S phase cells when fused with mitotic cells underwent premature chromosome condensation (PCC) that resulted in a pulverized morphology. Therefore, electron microscopy was used to examine the ultra-structure of chromosomes after different drug treatments (FIG. 5C). In control cells, as well as from mitotic cells obtained after treatment with BDM 50 µM+UCN-01, intact chromosomes were clearly visualized. However, mitotic cells generated by the treatment of BDM 200 µM+UCN-01 were highly fragmented.

Example 7

Summary

The studies described in the preceding Examples show that BDM can induce an S or G2 cell cycle arrest, depending on the concentration. This effect was not idiosyncratic of Hela cells, as the same effect was observed in cell lines derived from pancreatic, breast and ovarian cancers, at similar concentrations of BDM. Only a four-fold difference (50 and 200 µM for adherent cells, 10 and 50 uM for lymphoblast) in concentration can change the cell cycle response from a G2 to an S phase arrest.

The maximum concentration of BDM used in this study, 200 µM, to elicit cell cycle perturbations in 'solid' cancer cell lines, is consistent with the $IC_{50}$ values previously obtained. While 200 µM is ~8-13 times higher than clinically achieved, the lymphoma cell line U2932 did show the same dose-dependent cell cycle arrest at more clinically relevant concentrations of BDM; cells treated with 10 µM BDM resulted in a G2 arrest, while 25 µM BDM resulted in an S phase arrest. These findings suggest that the biological targets from hematologic malignancies may be more sensitive than cell lines derived from solid tumors to BDM.

The Examples show that BDM at 50 µM and 200 µM have distinct effects on cell cycle and induction of DNA damage. Notably, the repair capacity after treatment with 50 µM and 200 µM are distinct: after 48 h continuous exposure cells treated with 50 µM BDM exhibited no discernable markers of DNA damage, indicating that the damage was efficiently repaired. Moreover, cells were no longer arrested in G2 but were cycling normally, further suggesting repair of DNA damage. In contrast, cells treated with 200 µM BDM for 48 h failed to repair the damage, had persistent γ-H2AX foci and sustained cell cycle arrest.

These data support the notion that DNA damage induced by 200 µM BDM is repaired much less efficiently than at 50 µM. Furthermore, these findings are consistent with observations that not only does BDM induce more DNA double strand breaks as compared to the alkylating agents cyclophosphamide and BCNU, but also the BDM-induced damage is not repaired as efficiently as these two drugs.

Without intending to be limited to any particular theory or mechanism of action, it is believed that these data imply that short term exposure (24-48 h) to BDM at 50 µM induces transient DNA damage which the cell eventually repairs, leading to no discernable long-term effects as determined by clonogenic survival assays. At 200 uM BDM, damage is not repaired and a 95% reduction in clonogenic survival.

Using short-term assays, 48 h continuous exposure to BDM up to 200 µM did not reduce cell viability as compared to control treatment. Thus, the time and concentration of BDM is sufficient to activate cell cycle arrest but not trigger apoptosis. Cell cycle arrest with 200 µM BDM presented the opportunity to test the effect of Chk1 inhibition.

It was shown that the inhibition of Chk1, but not Chk2, enhanced killing of BDM-treated Hela in a short term assay. Sensitization by Chk1 inhibitors only occurred with 200 µM of BDM, the dose that elicited an S phase arrest. Using a combination of live-cell video-microscopy, metaphase spreads and EM, it was shown that the majority cells exhibiting these extremely abnormal mitoses end up dying in mitosis. It is believed that by killing cells in mitosis, this combinatorial treatment could reduce the number of cells that divide, survive, and potentially become refractory to treatment.

Example 8

Figure 6:
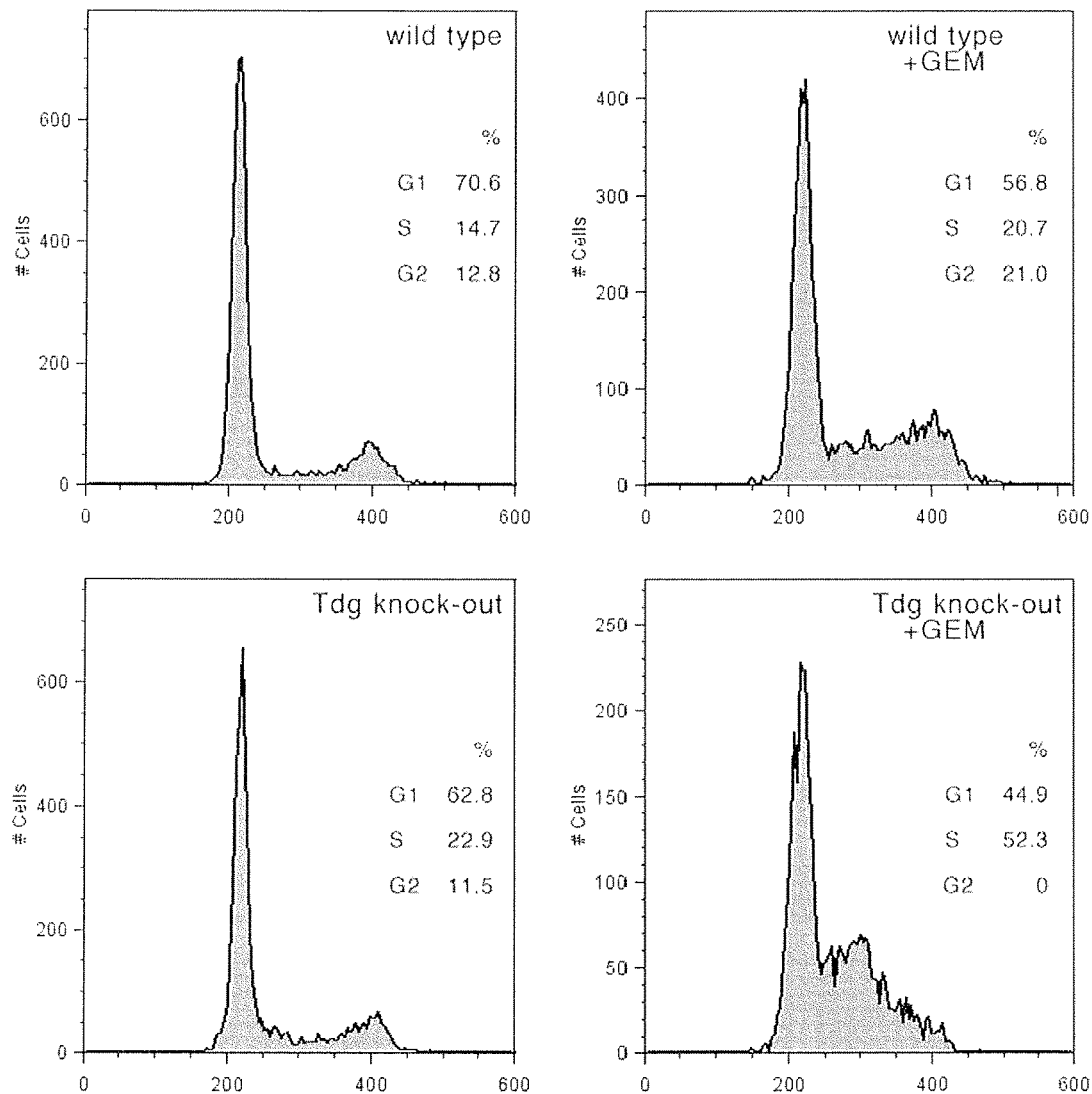
FIG. 6 shows cell cycle analysis by FACS of wild type and TDG null knock-out MEFs treated with Gemcitabine. The percent of cells in G1, S, and G2 phase is indicated.

Lack of Thymine DNA Glycosylase or Thymine DNA Glycosylase Activity Sensitizes Cells to Gemcitabine Isogenic, littermate-derived, thymine DNA glycosylase (TDG) wild type and knock-out mouse embryo fibroblast lines (MEFs) were treated with a sub-lethal dose of 50 nM gemcitabine for 48 hours. At the end of the treatment, cells were collected, stained with propidium iodide and analyzed by flow cytometry. The results revealed a dramatically increased sensitivity of TDG knock-out cells compared to wild type cells, with a prominent arrest in S phase (20.7% vs 52.3%. FIG. 6).

Figure 7:
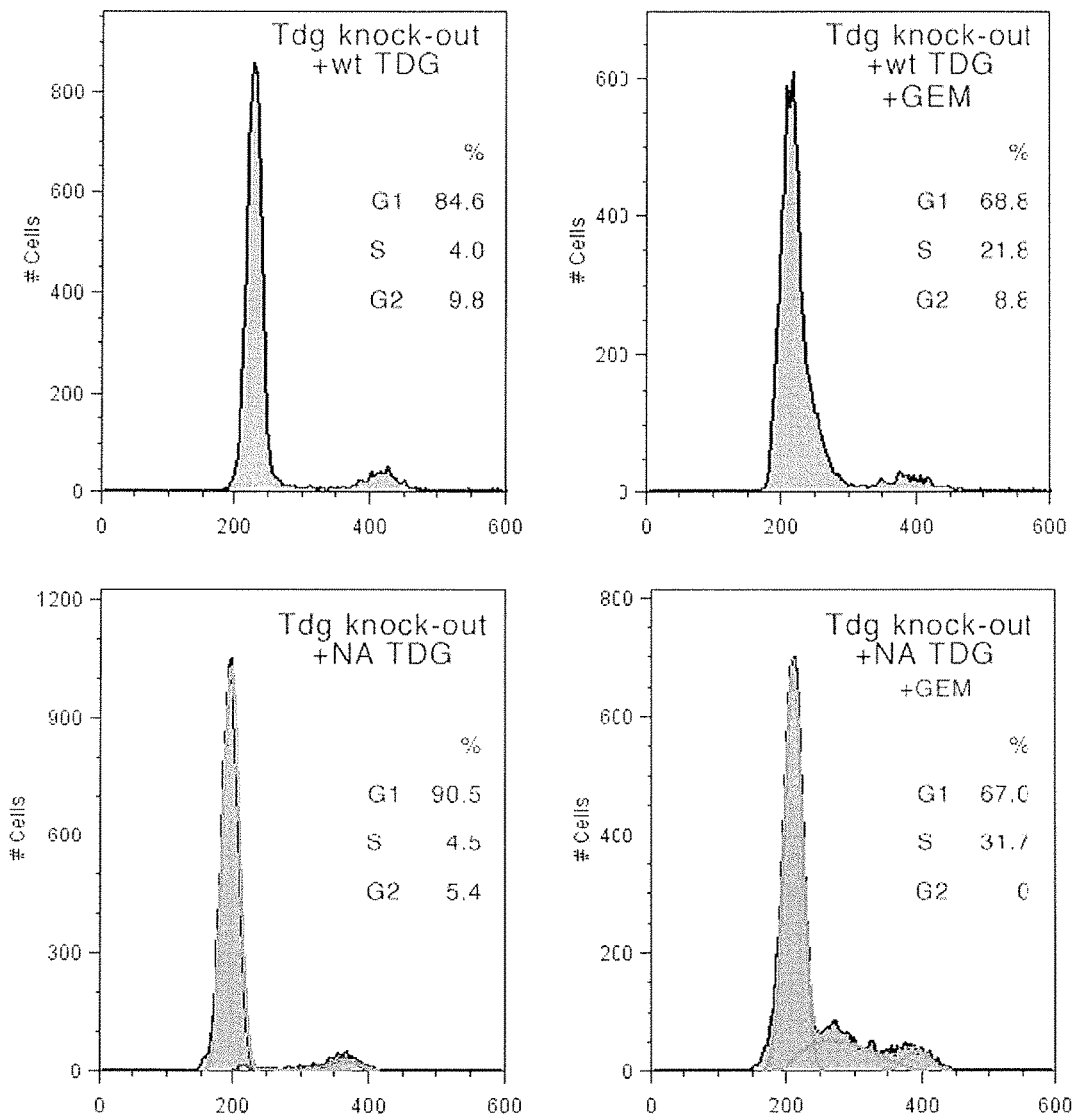
FIG. 7 shows cell cycle analysis by FACS of TDG null knockout MEFs transduced with wild type hTDG cDNA or N140A glycosylase-dead hTDG cDNA, and treated with Gemcitabine. The percent of cells in G1, S, and G2 phase is indicated.

The biologic function of TDG includes a non-enzymatic role as transcriptional co-activator, mediated by protein-protein interactions, and an enzymatic role related to its DNA N-glycosylase activity. To determine whether sensitization to gemcitabine was due to inactivation of TDG enzymatic function, TDG knock-out MEFs transduced with wild type or glycosylase-dead human TDG cDNA were evaluated. Flow cytometric analysis showed that knockout MEFs reconstituted with the wild type TDG responded the same as wild type MEFs to gemcitabine (FIG. 7). On the other hand, knock-out MEFs transduced with glycosylase-dead human TDG cDNA showed increased sensitivity to Gem in comparison to knock-out cells transduced with wild type human TDG cDNA (FIG. 7). It is believed that these results, when taken together, show that TDG catalytic activity is involved in cellular resistance to gemcitabine and its inactivation sensitizes cells to Gem, producing a prominent S phase arrest.

Example 9

TDG has Glycosylase Activity on 5-Hydroxymethyluracil

During studies on the role of TDG in development, two pathways for active DNA demethylation were identified based on linked deamination-base excision repair by TDG. In the first pathway, 5-methylcytosine is deaminated to thymine by deaminases of the AID/APOBEC family generating a G:T mismatch. In the second pathway, 5-hydroxymethylcytosine, an oxidation product of 5-methylcytosine, is deaminated to 5-hydroxymethyluracil (hmU), generating a G:hmU mismatch. While two other base excision repair glycosylases, methyl-CpG-binding domain protein 4 (MBD4, a.k.a. MED1) and single-strand selective monofunctional uracil DNA glycosylase (SMUG1) are efficient in removal of the mismatched T and hmU, respectively, it is believed that TDG appears to be the only glycosylase with strong activity on both deaminated bases (FIG. 8).

Example 10

Investigation of Synergy Between Gemcitabine and Thymine DNA Glycosylase Inhibition This is a prophetic example. These experiments will be undertaken to investigate improvements in gemcitabine cytotoxicity by inhibiting TDG glycosylase activity. A first set of experiments will screen two chemical libraries to identify TDG inhibitors. A second set of experiments will then investigate cytotoxicity of the candidate inhibitors, alone or in combination with gemcitabine Preliminary experiments determined that TDG plays a role in gemcitabine cytotoxicity. Lack of TDG (FIG. 7) or TDG catalytic activity (FIG. 6) leads to sensitization to gemcitabine, provoking a prominent S phase arrest. It is believed that the development of inhibitors of TDG glycosylase activity and their use in combination with gemcitabine may be a viable approach to improve gemcitabine efficacy.

Library screen: Two combined libraries of chemical compounds will be screened; one library includes 1,514 FDA-approved drugs and the other library includes 480 known bioactive compounds. For the screening, a standard radioactive DNA N-glycosylase assay will be used, which affords a small reaction volume (10-20 µl), high sensitivity and relatively high processivity (more than 50 reactions per gel, e.g., approximately 40 gels to screen 2000 compounds). Recombinant TDG protein produced in bacteria will be used—G:T mismatch-containing double-stranded oligonucleotide substrates, $P^{32}$-labeled at the 5' end of the T-containing strand, and library compounds will be screened at an initial dose of 10 µM (since TDG is 1 µM in the reaction, this represents an approximate 10-fold molar ratio between drug and enzyme). After running the reactions in sequencing gels to achieve separation of the substrate and product bands, TDG activity in the presence of the various compounds will be scored by comparison to the "no protein" and "no compound addition" controls (e.g., FIG. 8). negative and positive controls, respectively). For compounds showing inhibition of TDG, the screen will be repeated using lower concentrations of the candidate, up to an approximate molar ratio of 1 between drug and enzyme.

Candidate compounds will undergo additional testing in cell culture experiments. Cell extracts for repair assays will be prepared from wild type and TDG knock-out MEFs treated with various concentrations of the candidate inhibitor in order to determine whether the inhibitor affects G:T mismatch repair activity in a TDG-dependent manner. Cytotoxicity experiments will be conducted thereafter, with the candidate inhibitor alone and in combination with gemcitabine. Candidate compounds will be tested on wild type and TDG knock-out MEFs, to determine whether they have cytotoxic properties on their own and whether their cytotoxicity is TDG-dependent. Both cytotoxic and non-cytotoxic compounds will be used in combination with a sub-lethal dose of gemcitabine in short-term viability (MU) assays to assess cooperativity or synergy with gemcitabine. Compounds showing synergistic activity with gemcitabine will be further evaluated by flow cytometry to determine whether the combination treatment would induce an S-phase arrest.

A catalytically inactive TDG will be used as the reference for comparing reductions in the repair activities in the presence of compounds. By conducting the screen in duplicate, the chances of false hits should be reduced. Assays on compounds that do not replicate can be repeated, but chemical structures can be compared with validated hits to see if they might be structurally related. Given that the library contains a broad range of chemical structures, it is believed that an inhibitor or related inhibitors will likely be identified. The use of cell extracts will directly test the ability of candidate compounds to act in a cellular context. Cell extracts may be used to combat cell permeability issues that may preclude testing candidate compounds in cells. Positive hits from the cell extract experiments, which are negative in the cell viability experiments would indicate a permeability issue.

It is possible that compound concentrations will need to be enhanced in the screening assays in order to obtain a hit. The threshold will be 50 µM of drug, because higher concentrations would increase the chances of off-target effects in cell extracts or in cells. Additional studies may screen libraries containing uncharacterized/unknown compounds, also and a high-throughput screening assay is under development for this purpose.

Example 11

TDG Inactivation on HmdUrd Cytotoxicity+/−Gemcitabine

This is a prophetic example. Because the cytotoxic drug 5-hydroxymethyl-2'-deoxyuridine (HmdUrd) is incorporated in DNA as hmU, it is believed that HmdUrd cytotoxicity may also be mediated by TDG. The possibility will be investigated in these experiments.

Figure 9:
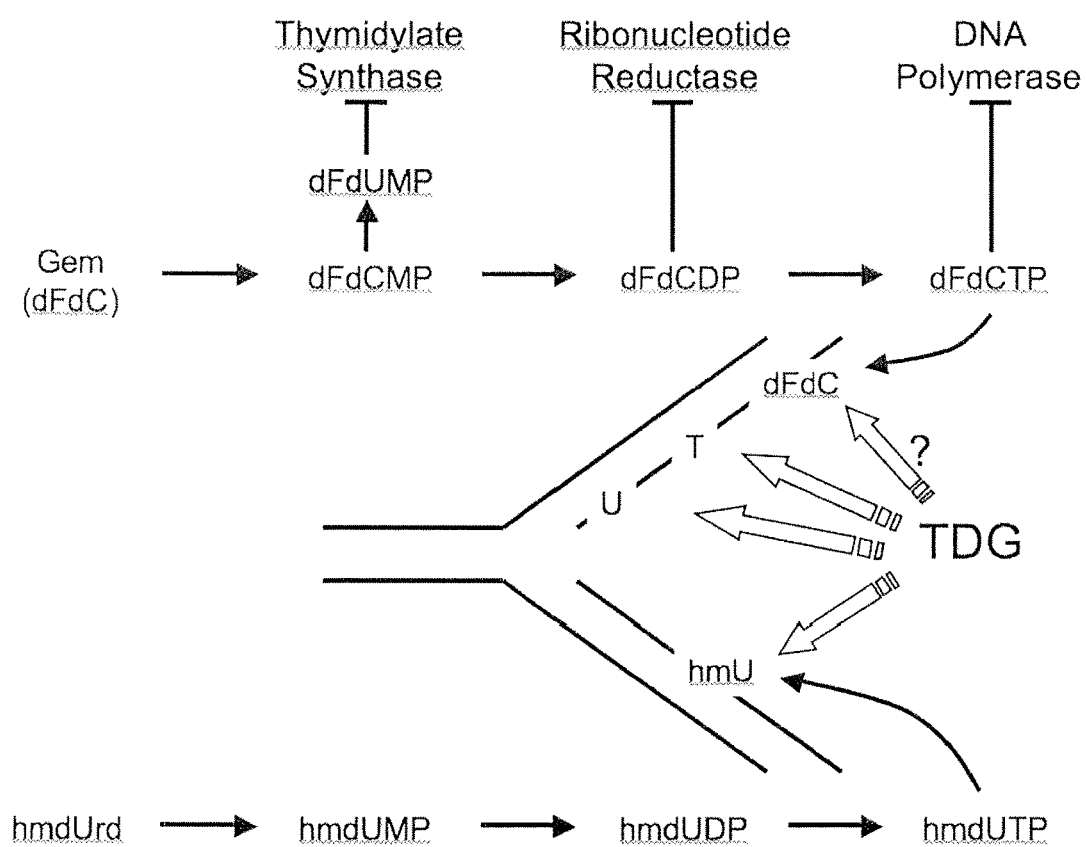
FIG. 9 shows proposed mechanisms of action of Gemcitabine and hmdUrd. It is believed that nucleotide pool imbalance caused by Gem leads to misincorporation of dUTP, dTTP and hmdUTP, whose bases are known TDG substrates.

The sensitivity of wild type and TDG-knockout MEFs to HmdUrd will first be investigated. Next, whether HmdUrd treatment can have cooperative or synergistic activity with gemcitabine will be investigated. These experiments are based, in part on the observation that TDG has robust glycosylase activity on 5-hydroxymethyluracil (5hmU), a base that would result from incorporation into genomic DNA of hmdUTP, the triphosphate nucleotide of HmdUrd (FIG. 9). It is believed that HmdUrd and gemcitabine can have synergistic activity because the nucleotide pool imbalance generated by gemcitabine is likely to favor incorporation of hmdUTP (FIG. 9). It is believed that given the role of TDG in 5hmU removal, it is possible that TDG inactivation may increase not only gemcitabine, but also HmdUrd cytotoxicity Preliminary experiments (FIG. 8A) indicated that like (SMUG1), TDG has glycosylase activity on hmU. HmU is an endogenous deamination product of 5-hmC in a pathway of DNA demethylation. Due to its activity, TDG represents a candidate target as a determinant of HmdUrd cytotoxicity. It is believed that combining treatment with gemcitabine administration will be beneficial because the two drugs are likely to require different DNA repair pathways such that tumor cells may not be able to process the damage induced by two drugs, as opposed to a single drug.

First, wild type and TDG knock-out cells will be treated with increasing concentration of HmdUrd, and toxicity will be assessed with MIT assays. Comparison between the two lines will a determination as to whether the toxicity is TDG-dependent. Next, the cooperativity or synergy of HmdUrd and gemcitabine treatment will be tested using the approach outlined in Example 10. Furthermore, if the search of TDG inhibitors in Example 10 is successful, candidate compounds will also be tested in combination with HmdUrd treatment.

It is possible that TDG may play a role in hmU removal (more than SMUG1) and, as such, TDG knock-out cells may be extraordinarily sensitive to HmdUrd treatment. On the other hand, if hmU recognition and removal by TDG activates a DNA damage response pathway leading to cell cycle arrest and apoptosis, TDG knock-out cells may be resistant to HmdUrd treatment.

Example 12

Small Molecule TDG Inhibitors Reduce Cell Viability and Clonogenic Capacity

Figure 10:
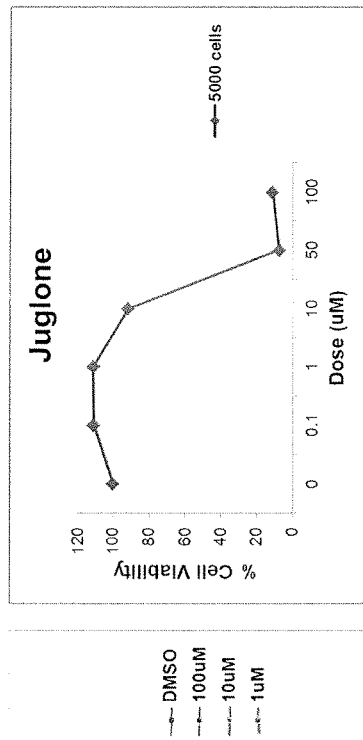
FIG. 10 shows inhibition of TDG glycosylase activity in vitro by juglone, and reduction of SK28 cell viability (MTS assay) and colony-forming ability (clonogenic assay) upon treatment with juglone.
Figure 10:
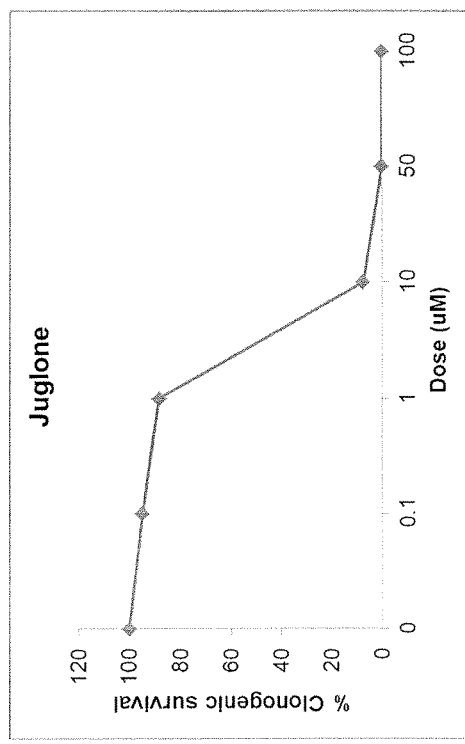
Figure 10:
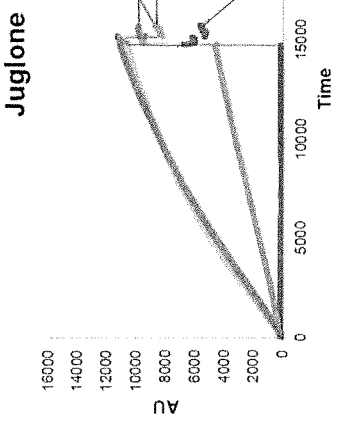
Figure 11:
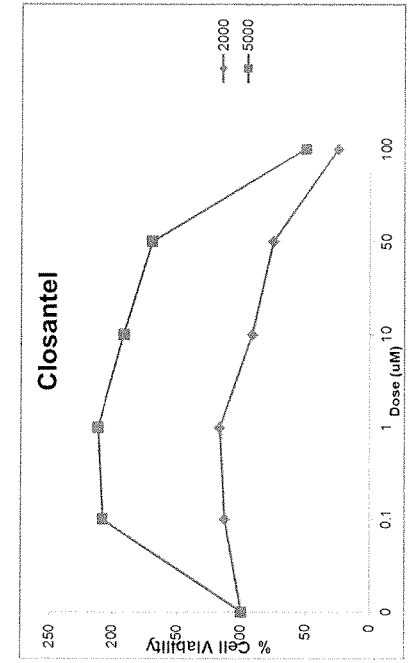
FIG. 11 shows inhibition of TDG glycosylase activity in vitro by closantel, and reduction of SK28 cell viability (MTS assay) and colony-forming ability (clonogenic assay) upon treatment with closantel.
Figure 11:
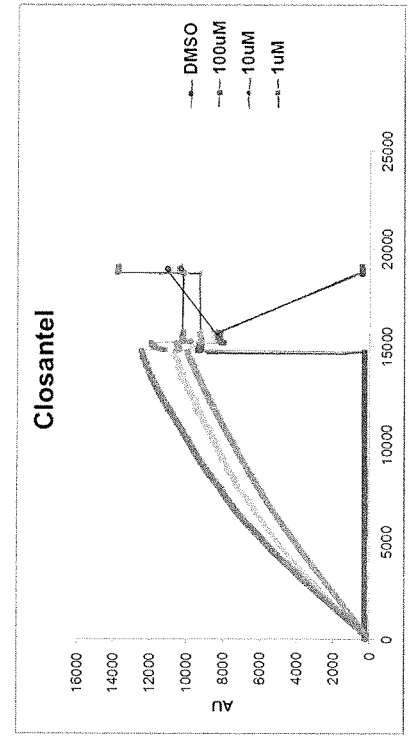
Figure 11:
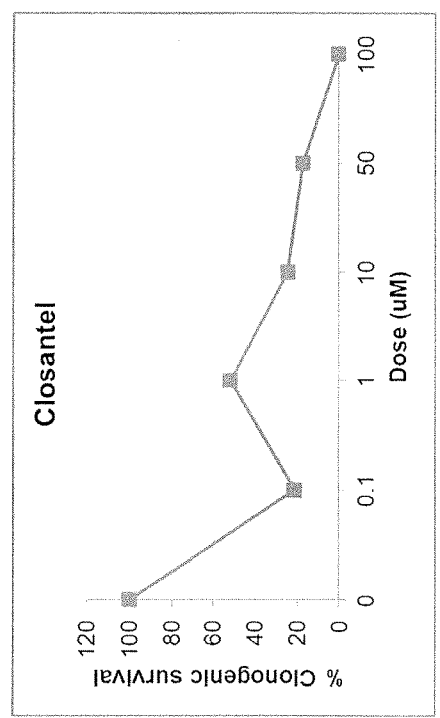
Figure 12:
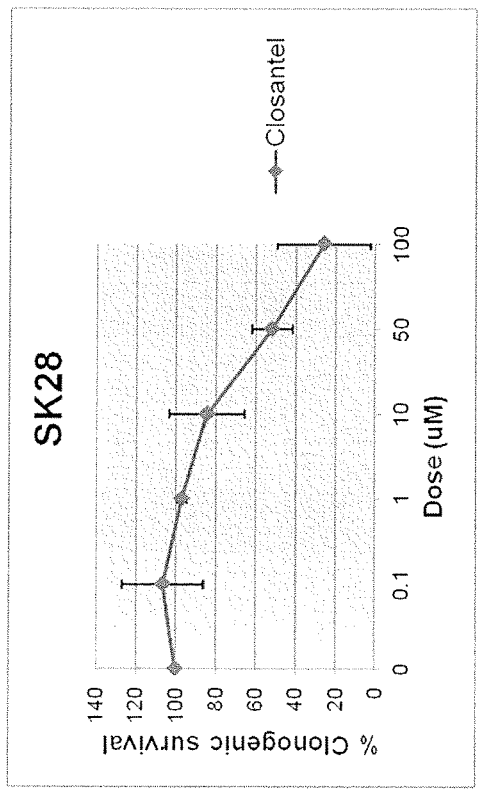
FIG. 12 shows a reduction of clonogenic capacity of SK28 MEL melanoma cells by juglone, closantel, and cefixime.
Figure 12:
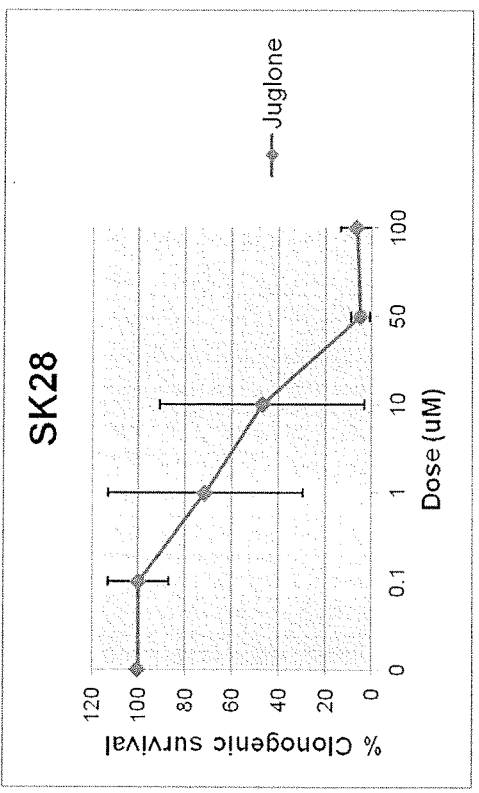
Figure 12:
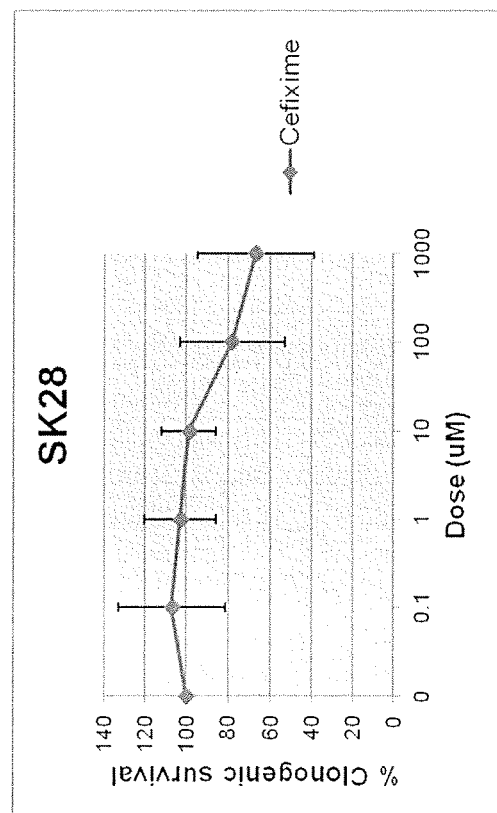

Juglone, a quinone chemopreventive agent extracted from the black walnut, closantel, an anti-helminth drug, and cefixime, an antibiotic from the cephalosporin family were found to reduce cell viability and clonogenic capacity of SK28 cells in a concentration-dependent fashion (FIG. 10, FIG. 11, and FIG. 12). Tests were conducted in quadruplicate.

Example 13

TDG Downregulation Increases Inhibition of Colony Formation by Gemcitabine (Gem)

Figure 13:
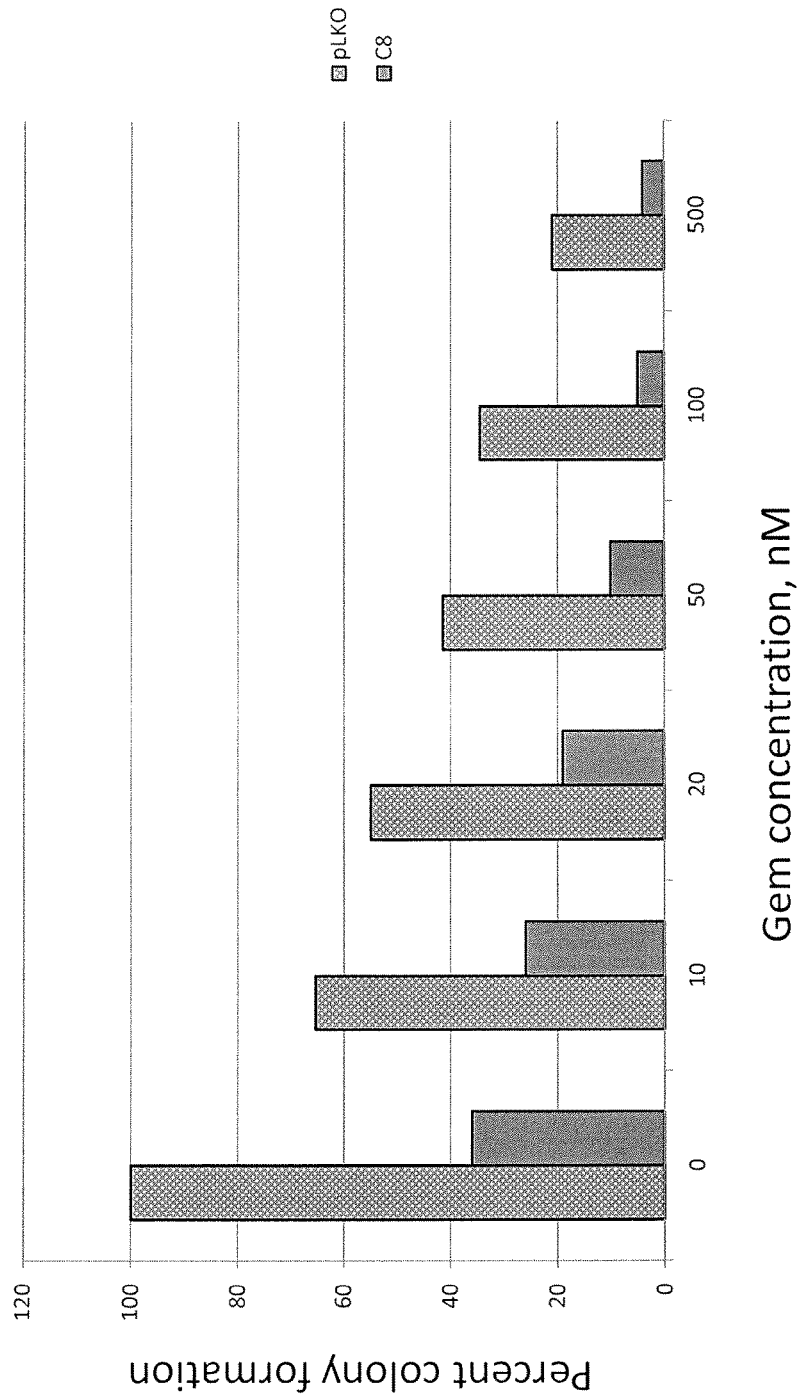
FIG. 13 shows BxPC3 pancreatic cancer cells are sensitized to gemcitabine after knockdown of TDG.

Clonogenic assays were conducted on pancreatic cancer (PaC) cell line BxPC3 infected with empty pLKO vector or with the C8 lentivirus that downregulates TDG. Even in the absence of gemcitabine, colony formation by the TDG knockdown cells was reduced nearly 60% (FIG. 13). In FIG. 10, the maximum number of colonies formed by pLKO-infected BxPC3 cells was set as 100%. Upon addition of increasing concentration of gemcitabine, colony formation of TDG knockdown cells was further reduced, and this reduction was greater than pLKO-infected cells expressing TDG. Thus, combined inhibition of TDG and gemcitabine treatment increased killing of BxPC3 cells relative to gemcitabine treatment alone.

Example 14

Figure 14:
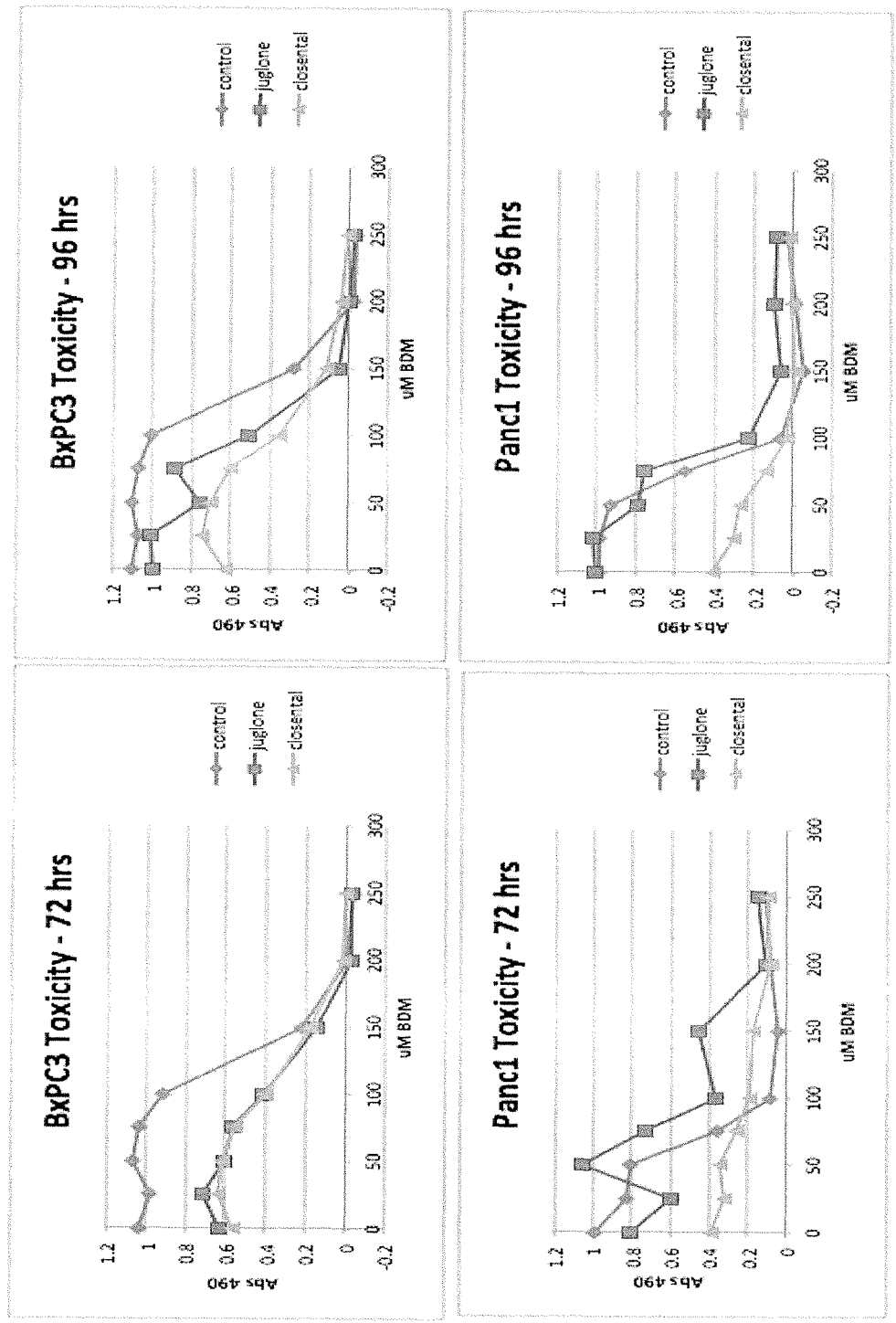
FIG. 14 shows BxPC3 and Panc1 toxicity at 72 hours (left panels) and at 96 hours (right panels).

Candidate TDG Inhibitors Juglone and Closantel Show a Synergistic Effect in Combination with Bendamustine (BDM) and Gemcitabine (Gem) in MTS Assays Two TDG inhibitors, juglone and closantel, were tested for their ability to kill two PaC cell lines, BxPC3 and Panc1 cells, in MTS assays. Cells were treated for 72 and 96 hours with 10 µM juglone and 20 µM closantel, in combination with increasing concentrations of BDM. The results revealed that closantel shows a synergistic killing effect in combination with BDM in both cell lines, ands juglone shows a synergistic killing effect in combination with BDM in BxPC3 (FIG. 14).

Figure 15:
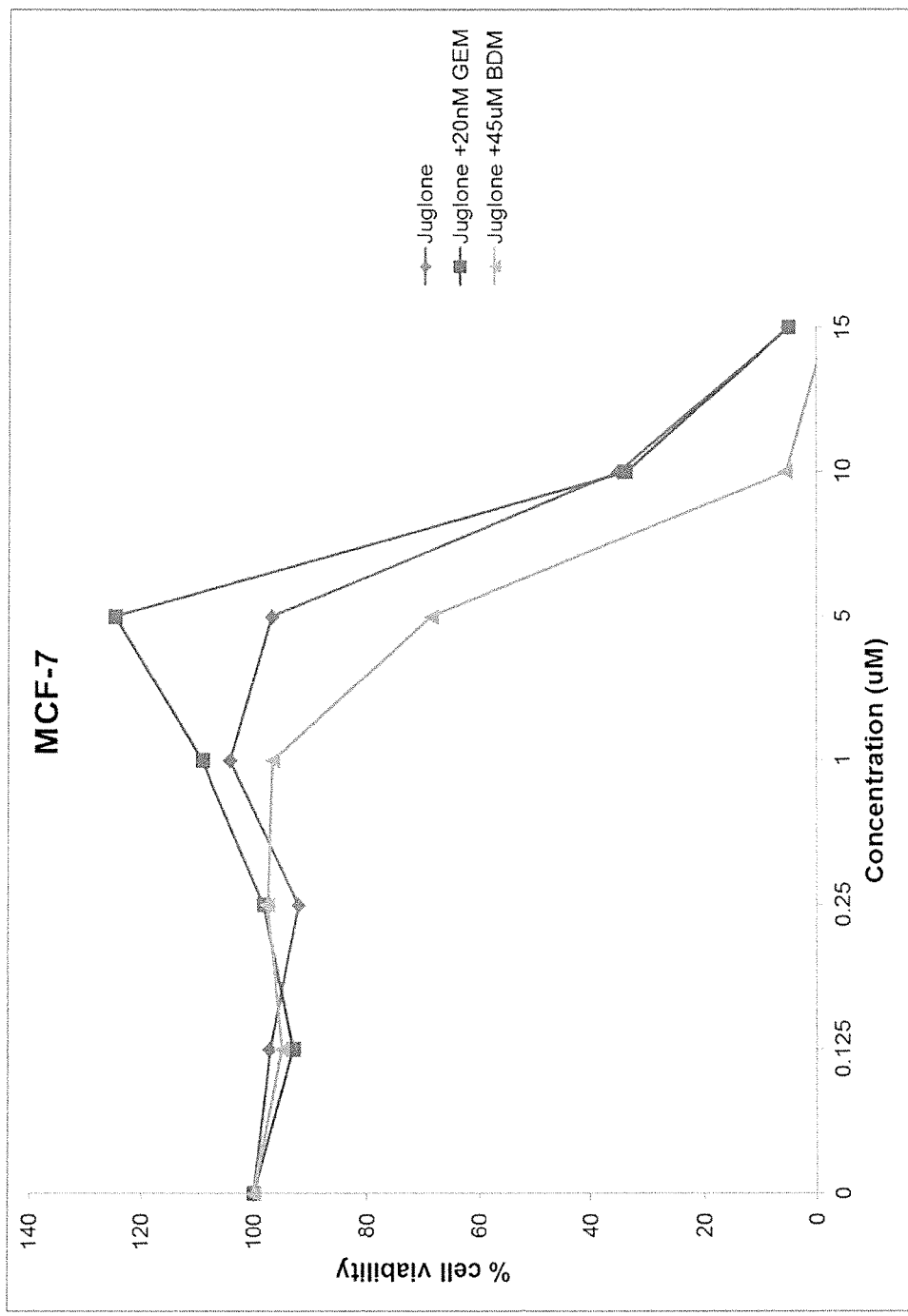
FIG. 15 shows synergistic killing of MCF-7 cells with juglone combined with gemcitabine (squares) and with bendamustine (triangles).
Figure 16:
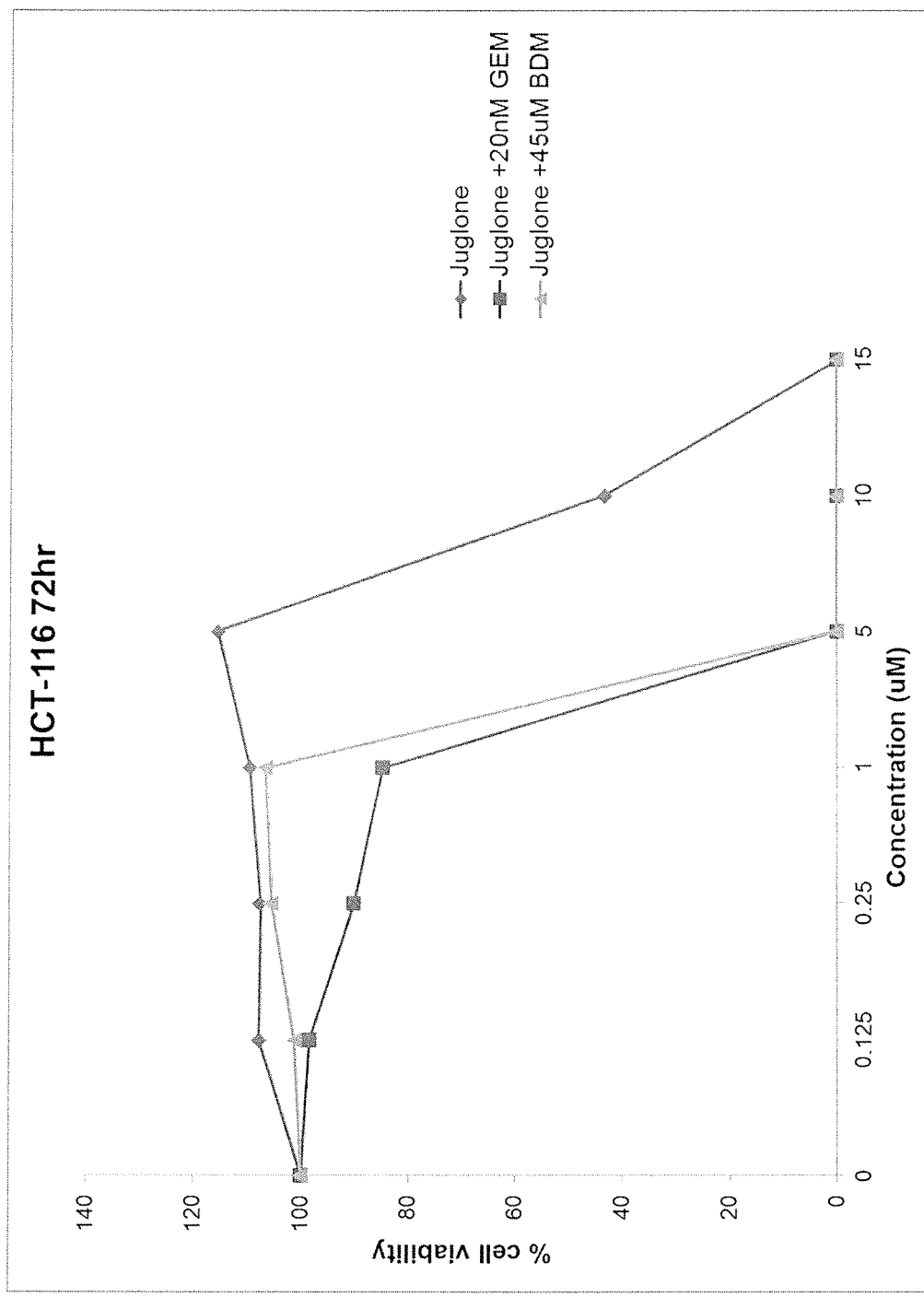
FIG. 16 shows synergistic killing of HCT-116 cells with juglone combined with gemcitabine (squares) and with bendamustine (triangles).
Figure 17:
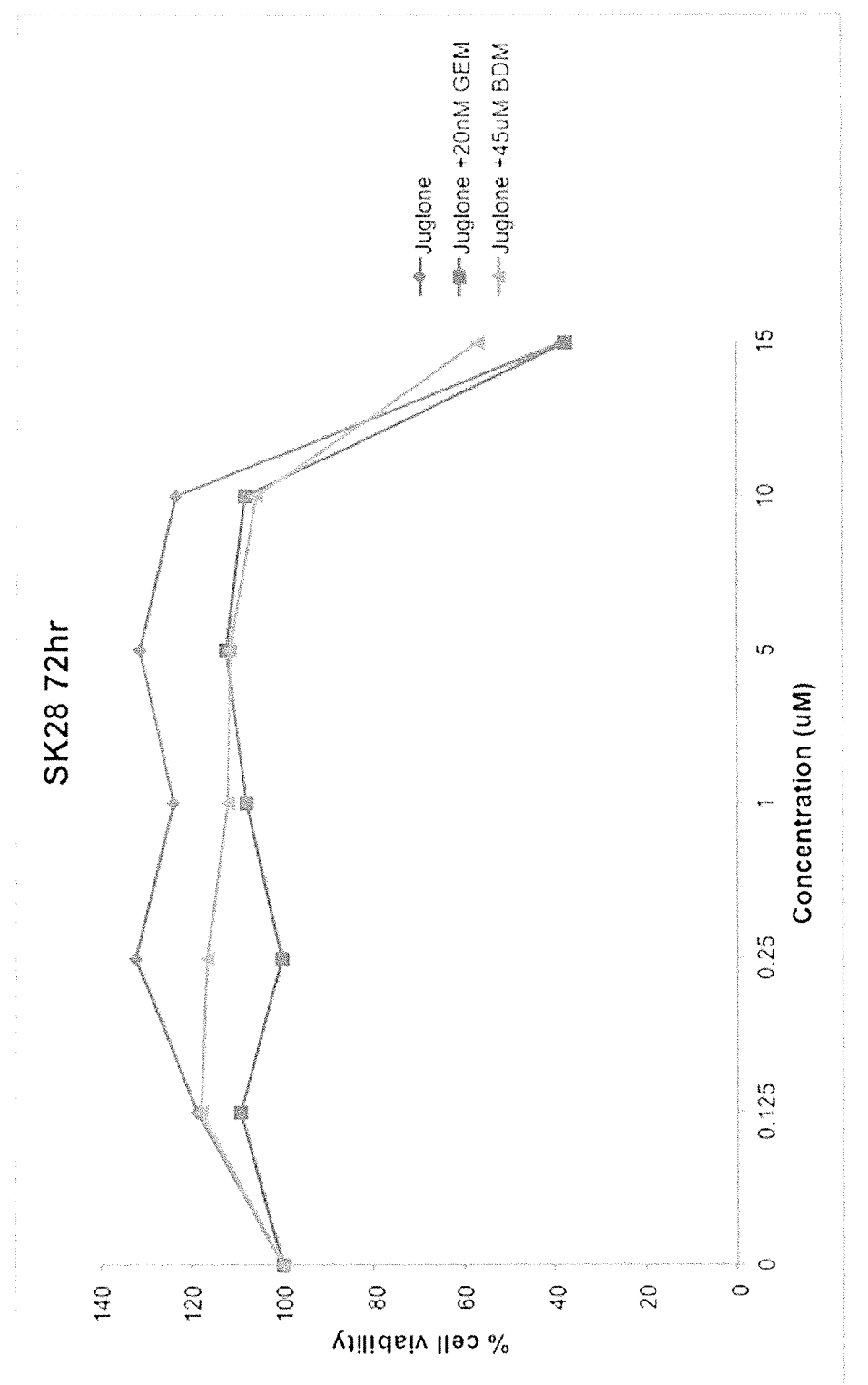
FIG. 17 shows synergistic killing of SK28 cells with juglone combined with gemcitabine (squares) and with bendamustine (triangles).

A similar synergistic effect of the combination of juglone and BDM was observed for MCF7 breast cancer cells (FIG. 15). In addition, both HCT116 colon cancer cells (FIG. 16) and SK28 melanoma cells (FIG. 17) were more effectively killed by combinations of juglone and gemcitabine, as well as juglone and bendamustine.

Example 15

Figure 18:
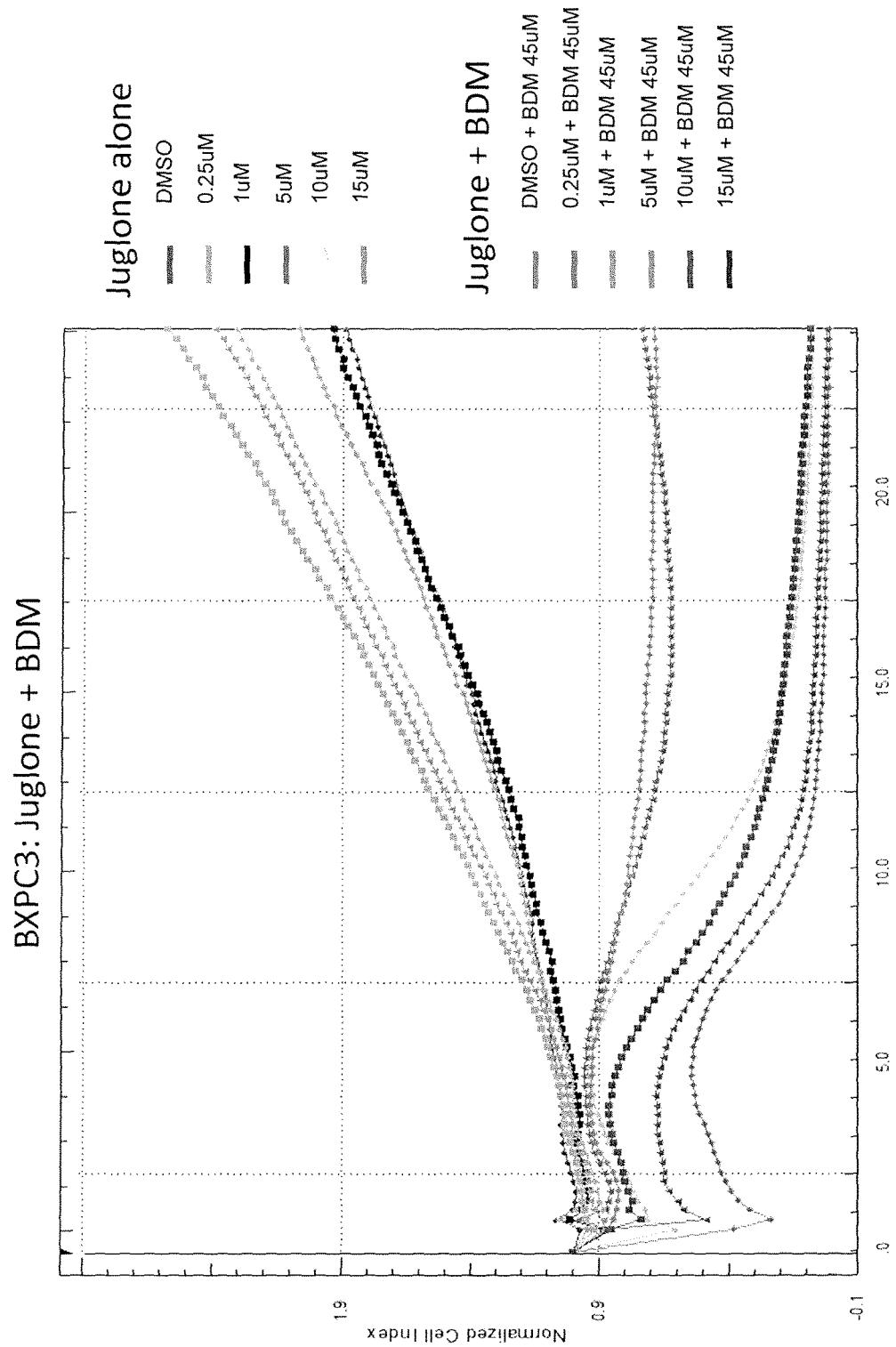
FIG. 18 shows the normalized cell index for BxPC3 cells treated with juglone and bendamustine, and illustrates a reduction of proliferation and increased killing of the cells with this combination of juglone and bendamustine, relative to juglone alone.
Figure 19:
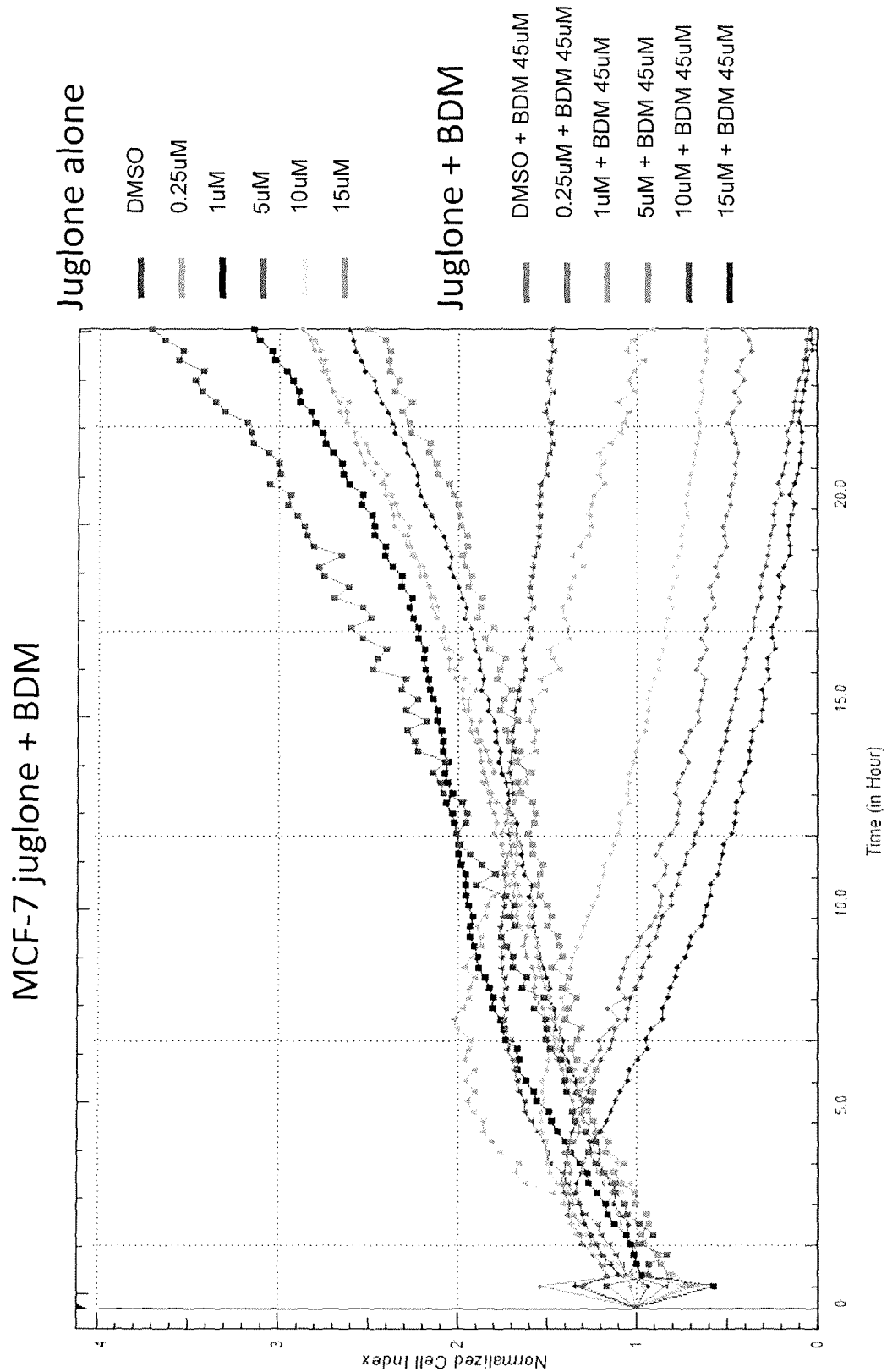
FIG. 19 shows the normalized cell index for MCF-7 cells treated with juglone and bendamustine, and illustrates a reduction of proliferation and increased killing of the cells with this combination of juglone and bendamustine, relative to juglone alone.

Candidate TDG Inhibitor Juglone Shows a Synergistic Effect in Combination with Bendamustine (BDM) in xCelligence Proliferation Assays To independently verify the MTS and clonogenic assays described in the preceding Examples, an assay was conducted using a xCelligence real-time cell analyzer (ACEA Biosciences, Inc.), using a label-free, non-invasive method to monitor adherent cell behavior, including proliferation, spreading and compound-mediated cytotoxicity. The system is based on detecting impedance differences within an electrical circuit created in microelectrodes at the base of culture wells; these differences are converted into a cell index (CI), a value that is influenced by a variety of factors, such as cell number, cell size and cell adhesion. The effect of the TDG inhibitor juglone, in combination with bendamustine (BDM) and gemcitabine (GCB), was assessed on the growth of various cancer cells. BxPC3 cells were treated with 45 µM BDM, in combination with increasing concentrations of juglone, and proliferation was followed over 24 hours. It was observed that treatment with juglone plus BDM suppressed proliferation more than juglone alone (FIG. 18). A similar result was observed with MCF7 breast cancer cell lines (FIG. 19).

The invention is not limited to the embodiments described and exemplified above, but is capable of variation and modification within the scope of the appended claims.

We claim:

1. A method for treating a pancreatic tumor or lung tumor that expresses thymine DNA glycosylase (TDG), comprising administering to a human patient having a pancreatic tumor or lung tumor that expresses TDG an effective amount of bendamustine or gemcitabine and an effective amount of juglone, cefixime, or closantel, thereby treating the tumor in the patient, wherein the combination produces synergistic killing of tumor cells.

2. The method of claim 1, wherein the tumor is a pancreatic tumor.

3. The method of claim 1, wherein the method comprises administering to the patient an effective amount of gemcitabine and an effective amount of juglone.

4. A method for treating a pancreatic tumor that expresses thymine DNA glycosylase (TDG), comprising administering to a human pancreatic cancer patient in need thereof an effective amount of bendamustine or gemcitabine in combination with an effective amount of a TDG inhibitor selected from the group consisting of juglone, closantel, and cefixime, thereby treating the pancreatic tumor in the patient, wherein the combination produces synergistic killing of pancreatic tumor cells.

5. The method of claim 4, wherein the method comprises administering to the patient an effective amount of bendamustine or gemcitabine in combination with an effective amount of juglone.

6. A method for treating a breast tumor that expresses thymine DNA glycosylase (TDG), comprising administering to a human breast cancer patient in need thereof an effective amount of bendamustine or gemcitabine in combination with an effective amount of a TDG inhibitor selected from the group consisting of juglone, closantel, and cefixime, thereby treating the breast tumor in the patient, wherein the combination produces synergistic killing of breast tumor cells.

7. The method of claim 6, wherein the method comprises administering to the patient an effective amount of bendamustine or gemcitabine in combination with an effective amount of juglone.

8. A method for treating melanoma expressing thymine DNA glycosylase (TDG), comprising administering to a human melanoma patient in need thereof an effective amount of bendamustine or gemcitabine in combination with an effective amount of a TDG inhibitor selected from the group consisting of juglone, closantel, and cefixime, thereby treating melanoma in the patient, wherein the combination produces synergistic killing of melanoma cells.

9. The method of claim 8, wherein the method comprises administering to the patient an effective amount of bendamustine or gemcitabine in combination with an effective amount of juglone.

10. The method of claim 1, wherein the tumor is a lung tumor.

11. The method of claim 6, wherein the method comprises administering the patient an effective amount of gemcitabine in combination with an effective amount of juglone.

12. The method of claim 1, further comprising administering a DNA base excision repair inhibitor to the human patient.

* * * * *

UNITED STATES PATENT AND TRADEMARK OFFICE
CERTIFICATE OF CORRECTION

PATENT NO. : 10,220,051 B2
APPLICATION NO. : 14/540428
DATED : March 5, 2019
INVENTOR(S) : Alfonso Bellacosa et al.

It is certified that error appears in the above-identified patent and that said Letters Patent is hereby corrected as shown below:

In the Specification

In Column 1, beginning on Line 16, replace the paragraph:
"REFERENCE TO GOVERNMENT GRANTS
This invention was made with government support under Grant Nos. GM86877 and CA078412 awarded by the National Institutes of Health and Grant No. W81XWH-11-1-0201 awarded by the U.S. Department of Defense ARMY/MRMC. The government has certain rights in the invention."

With:
--REFERENCE TO GOVERNMENT GRANTS
This invention was made with government support under W81XWH-11-1-0201 awarded by the Medical Research and Development Command, and GM086877 and CA078412 awarded by the National Institutes of Health. The government has certain rights in the invention.--

Signed and Sealed this
Twenty-ninth Day of August, 2023

Katherine Kelly Vidal
*Director of the United States Patent and Trademark Office*

SEQUENCE LISTING

<160> NUMBER OF SEQ ID NOS: 4

<210> SEQ ID NO 1
<211> LENGTH: 21
<212> TYPE: DNA
<213> ORGANISM: Homo sapiens

```
<400> SEQUENCE: 1
ccagcaggat ttaatggtat t                                         21

<210> SEQ ID NO 2
<211> LENGTH: 21
<212> TYPE: RNA
<213> ORGANISM: Homo sapiens

<400> SEQUENCE: 2
ccagcaggau uuaaugguau u                                         21

<210> SEQ ID NO 3
<211> LENGTH: 21
<212> TYPE: DNA
<213> ORGANISM: Homo sapiens

<400> SEQUENCE: 3
gccacgaata gcggtgttta a                                         21

<210> SEQ ID NO 4
<211> LENGTH: 21
<212> TYPE: RNA
<213> ORGANISM: Homo sapiens

<400> SEQUENCE: 4
gccacgaaua gcgguguuua a                                         21
```